US005629182A

United States Patent [19]
Chopin et al.

[11] Patent Number: 5,629,182
[45] Date of Patent: May 13, 1997

[54] DNA FRAGMENTS CODING FOR A BACTERIOPHAGE-RESISTANT MECHANISM

[75] Inventors: Marie-Christine Chopin, Paris, France; Pierre-Jean Cluzel, deceased, late of Lyon, France, by Hélène Cluzel, Jean Cluzel, executors

[73] Assignee: Institut National de la Recherche Agronamique (INRA), Paris, France

[21] Appl. No.: 248,466

[22] Filed: May 24, 1994

Related U.S. Application Data

[63] Continuation-in-part of Ser. No. 988,959, Mar. 15, 1993, abandoned.

[30] Foreign Application Priority Data

Sep. 14, 1990 [FR] France ................................ 90 11381

[51] Int. Cl.$^6$ .......................... C12N 15/31; C12N 1/21; C12N 15/74; C07H 21/04
[52] U.S. Cl. ............................. 435/172.3; 435/252.3; 435/320.1; 536/23.7; 536/24.32; 935/29
[58] Field of Search ................. 536/23.7, 24.32; 435/320.1, 252.3, 172.3; 530/350, 825; 935/55, 29

[56] References Cited

U.S. PATENT DOCUMENTS

| | | | |
|---|---|---|---|
| 4,931,396 | 6/1990 | Klaenhammer et al. | 435/320.1 |
| 5,019,506 | 5/1991 | Daly et al. | 435/320.1 |
| 5,139,950 | 8/1992 | Klaenhammer et al. | 435/320.1 |
| 5,459,072 | 10/1995 | McKay et al. | 435/320.1 |

FOREIGN PATENT DOCUMENTS

| | | |
|---|---|---|
| 0208468 | 1/1987 | European Pat. Off. . |
| 90/11381 | 9/1990 | France . |

OTHER PUBLICATIONS

Journal of Dairy Science, vol. 72, No. 12, 1989, (Champaign, Illinois, US), T.R. Klaenhammer: "Genetic Characterization of Multiple Mechanisms of Phage Defense From a Prototype Phage–Insensitive Strain, Lactococcus Lactis ME2", pp. 3429–3443.

Journal of Bacteriology, vol. 172, No. 8, Aug. 1990, D.A. Romero et al.: "Characterization of Insertion Sequence IS946, AN Iso–ISS1 Element, ISO; ATED From the Conjugative Lactoccocal Plasmid pTR2030", pp. 4151–4160.
Applied and Environmental Microbiology, vol. 56, No. 7, Jul. 1990, C. Hill et al.: "Nucleotide Sequence and Distribution of the pTR2030 Resistance Determinant (hsp) which Aborts Bacteriophage Infection in Lactococci", pp. 2255–2258.
Applied and Environmental Microbiology, vol. 55, No. 7, Jul. 1989, C. Hill et al.: "Localization Cloning and Expression of Genetic Determinants for Bacteriophage Resistance (hsp) From the Conjugative Plasmid pTR2030", pp. 1684–1689.
Biochimie, vol. 70, 1988 (Paris, FR), M.E. Sanders: "Phage Resistance in Lactic Acid Bacteria", pp. 411–421.
Coffey et al "Identification and characterization of a plasmid . . . " Neth. Milk Dairy J. 43:229–244 (1989).
Coffey et al "Cloning and characterization of the determinant . . . " J. Gen. Microbiol. 137:1355–1362 (Jun. 1991).
Gautier et al, "Plasmid—Determined Systems for . . . Abortive Infection in Streptococcus cremoris", Appl, Environ. Microbiol. 53(5):923–927 (May 1987).
Simon et al "Construction of a vector plasmid family . . . " Biochimie 70:559–566 (Apr. 1988).
Chopin et al "Two Plasmid—Determined . . . Systems in Streptococcus lactis" Plasmid 11:260–263 (May 1984).
Sing et al "Plasmid—Induced Abortive Infection in Lactococci : A Review" J. Dairy Science 73:2239–2251 (Sep. 1990).

Primary Examiner—Marianne P. Allen
Assistant Examiner—Robert C. Hayes
Attorney, Agent, or Firm—Oblon, Spivak, McClelland, Maier & Neustadt, P.C.

[57] ABSTRACT

The invention relates to DNA fragments encoding an Abi-type mechanism of resistance to bacteriophages, which fragments are capable of being obtained by cloning of chromosomal or plasmid DNA of a bacteriophage-resistant lactic acid bacterial strain, as well as to a polypeptide involved in an Abi-type resistance mechanism, encoded by one of the said fragments. The invention also encompasses recombinant vectors and transformed bacterial strains comprising the said DNA fragments.

18 Claims, 5 Drawing Sheets

DNA FRAGMENTS CODING FOR A BACTERIOPHAGE-RESISTANT MECHANISM

This application is a continuation-in-part of application Ser. No. 07/988,959 filed Mar. 15, 1993, now abandoned, which is a 371 of International Application No. PCT/FR91/00722 filed on Sep. 13, 1991.

BACKGROUND OF THE INVENTION

1. Field of the Invention

The invention relates to the cloning of DNA sequences carrying genes encoding mechanisms of resistance to phages in bacteria, in particular lactic acid bacteria.

2. Description of the Related Art

Some bacteria responsible for fermentations are very sensitive to attack by bacteriophages, which, given the importance of lactic acid fermentations in the food industry, presents a major economic problem. Numerous attempts have consequently been made for several years, in order to offer a solution to this problem.

It was proposed, in a first instance, to use in the fermentation, natural mutants or mutants obtained by mutagenesis, and selected for their resistance to bacteriophages. This approach is however considerably limited by the fact that, in most cases, these strains possess other characteristics which are unfavourable for their use, and which are, for example, a slow growth or alternatively the production of metabolites which alter the organoleptic qualities of the finished product. In addition, a reversion to the wild phenotype, and therefore a loss of resistance, or the appearance of sensitivity to other types of phages is frequently observed under the conditions of industrial use of these strains [GASSON and DAVIES, in Advances in the Microbiology and Biochemistry of Cheese and Fermented Milk, Davies F. L. & Law B. eds, 127–151, Elsevier Applied Science Publishers (1984)]. The consequence of this is that a very small number of mutant strains is in effect used industrially.

However, the study of these strains has made it possible to reveal the existence of several different mechanisms of resistance to phages.

Three principal mechanisms of resistance to phages have thus been described in the resistant strain *Lactococcus lactis* ME2 [KLAENHAMMER, J. Dairy Sci., 72, 3429–3443, (1989)].

In one of them, called "mechanism of interference with adsorption", the product of the resistance gene delays the absorption of the phage on the bacterium.

A second mechanism called "mechanism of restriction-modification" (R/M), calls into play a restriction endonuclease which degrades the phage DNA as soon as it enters the bacterium. However, this endonuclease is linked to a methylase which has the same specificity; it follows that some phage DNA modified by the methylase may escape the action of the endonuclease and give rise to infectious particles. Several R/M systems of differing specificities have been described; these systems have a variable efficiency: the frequency of appearance of viral particles containing a modified DNA is between $10^{-1}$ and $10^{-8}$. Under the conditions of industrial culture when during an infection very many viral particles appear, the efficiency of this system is therefore inadequate. However, when several R/M systems are present in the same bacterium, the protection offered appears more efficient [JOSEPHSEN and KLAENHAMMER, Plasmid, 23, 71–75 (1989)].

The genes encoding the R/M type mechanisms known so far are all located in the plasmid.

The third type of defense mechanism which has been described is called "mechanism of abortive infection" (Abi). In the bacterial strains which possess this type of mechanism, the adsorption of phages is normal, but the multiplication of phages to give rise to new viral particles occurs only in a few cells. Moreover, the phages resulting therefrom are not capable of producing a complete lytic cycle when they infect a new cell.

All the Abi type mechanisms described so far are encoded by genes carried by plasmids [MCKAY et al., Appl. Environ. Microbiol., 47, 68–74 (1984)]; [KLAENHAMMER and SANOZKY, J. Gen. Microbiol. 131, 1531–1541 (1985)]; [GAUTIER and CHOPIN, Appl. Environ. Microbiol. 53, 923–927 (1987)]; [DALY and FITZGERALD, in Streptococcal Genetics, Ferretti J. & Curtiss R. eds, III, 259–268 ASM, Washington D.C. (1987)]; [LAIBLE et al., J. Dairy Sci. 70., 2211–2219 (1987)]; [MURPHY et al., Appl. Environ. Microbiol. 54, 777–783 (1988)]; [JARVIS, Appl. Environ. Microbiol. 53, 777–783 (1988)]; [FROSETH et al., J. Dairy Sci. 71, 275–284 (1988)].

The gene encoding an Abi-type resistance mechanism, called Hsp, which is carried by the plasmid pTR2030 has been cloned and sequenced [HILL et al., Appl. Environ. Microbiol., 56, 2255–2258, (1990)].

The modes of action of the Abi-type resistance mechanisms have not yet been elucidated; it appears however that abortive infection may result from several systems having different mechanisms of action, active on different phages and, at different levels, on viral proliferation. It has for example been shown that the plasmid pTR2030 is more active on the phages belonging to the so-called group of "small phages with isometric heads" than on those belonging to the group of "big phages with isometric heads" or to the group of phages "with elongated heads".

Similar observations concerning a specific resistance to attack by a group of phages have been made for other plasmids carrying genes encoding Abi-type resistance mechanisms [DALY and FITZGERALD, (1987); FROSETH et al., (1988); MURPHY et al., (1988) (publications mentioned above); STEELE and MCKAY, Plasmid, 22, 32–43 (1989)].

However, other plasmids, for example the plasmid pIL105 [GAUTIER and CHOPIN, App. Environ. Microbiol., 53, 923–927 (1987)], and pAJ1106 [JARVIS, App. Environ. Microbiol. 54., 77–783 (1988)] encode Abi resistance mechanisms which have a different specificity from the preceding plasmids and are effective both on "isometric" phages and on phages "with elongated heads".

Other observations also show that several Abi-type resistance systems exist; hybridisation experiments between different Abi plasmids have suggested that different loci were involved [STEELE et al., Appl. Environ. Microbiol., 55, 2410–2413 (1989)]. It has also been observed that the resistance to phages was increased when several DNA sequences encoding Abi mechanisms were linked.

The use of plasmids encoding mechanisms for resistance to phages to transfer this resistance to the strains used in industry has been proposed. For example, bacterial strains containing the autotransferable plasmid pTR2030 have been successfully used in industrial fermentations, and they exhibited satisfactory resistance to bacteriophage attack, which shows the real usefulness of Abi-type resistance genes.

However, the plasmid pTR2030 like most phage resistance plasmids described in the prior art and whose use has been suggested, is a "natural" plasmid present in resistant strains and transmitted to other strains by bacterial conjugation. The use of such plasmids has certain limits; these plasmids should be transferable or they should be capable of being linked to a plasmid vector; they should also be stable inside the host bacterium and should not contain genes which modify its phenotype in an unfavourable manner; furthermore, in order to be able to combine in the same bacterium-various mechanisms of resistance to phages, the plasmids concerned should be mutually compatible. Finally, this technique does not enable the transfer of resistance genes which may be carried, not by the plasmid DNA, but by chromosomal DNA. It is therefore particularly desirable to clone the genes responsible for these resistance mechanisms so as to be able to insert them at will inside suitable recombinant vectors which are mutually compatible and which are compatible with the host bacterium whose transformation is desired.

SUMMARY OF THE INVENTION

Figure 1:
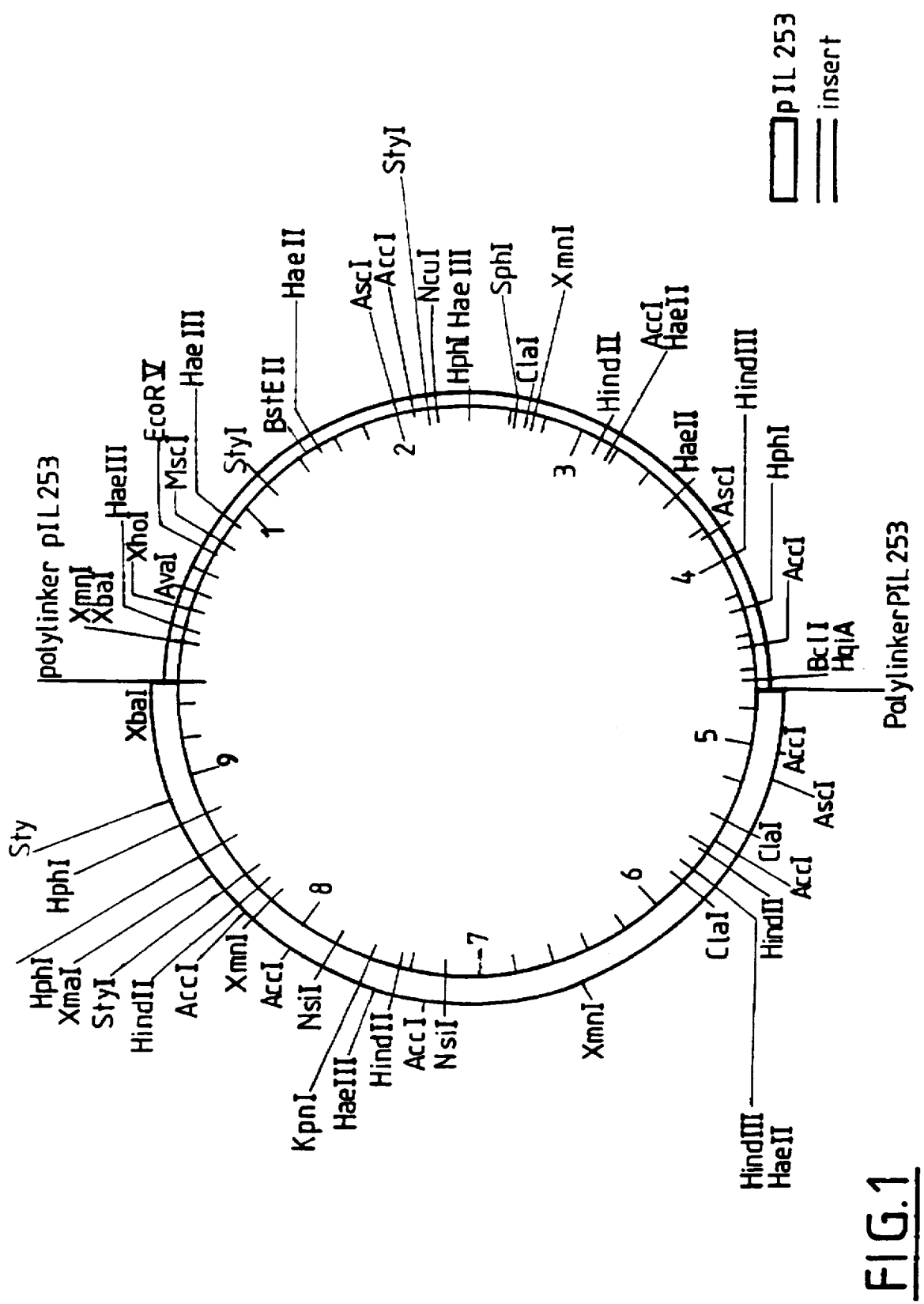
FIG. 1 shows the restriction map of the pIL353 plasmid.

The aim of the present invention is to detect and clone DNA sequences encoding mechanisms of resistance to attack by bacteriophages, and to produce recombinant plasmids comprising these genes and enabling their transfer and their expression in bacterial strains involved in industrial fermentations.

The present invention relates to DNA fragments comprising at least one gene encoding an Abi-type mechanism of resistance to bacteriophages, characterised in that they comprise a sequence homologous to that of all or part of at least one fragment chosen from the group consisting of:

the fragment encoding the resistance mechanism called Abi 416, the sequence of which is presented in the list of sequences in the appendix under the number SEQ ID NO: 1.

This fragment represents a portion of a fragment SPhI-EcoRI of about 2 kb, of the plasmid pIL353, which fragment is cloned from the DNA of *L. lactis ssp lactis* IL416.

the insert of about 9.4 kb, of the plasmid pIL352, which insert is cloned from the total DNA of the strain IL420 of *L. lactis ssp cremoris*, and comprises at least one gene encoding the resistance mechanism called Abi 420. SEQ ID NO: 13 is the sub-fragment of the 9.4 kb insert of pIL352 which encodes Abi 420; SEQ ID NO: 14 and SEQ ID NO: 15 represent the corresponding polypeptides.

the fragment whose partial sequence is presented in the list of sequences under the number SEQ ID NO: 4;

the fragment whose sequence is presented in the list of sequences under the number SEQ ID NO: 5.

The sequences SEQ ID NO: 3, SEQ ID NO: 4 and SEQ ID NO: 6, constitute open reading frames called ORF2, ORF3 and ORF1 respectively.

The invention encompasses also the insert of about 5.7 kb, of the plasmid pIL618, whose partial sequence is presented in the list of sequences in the appendix under the number SEQ ID NOS: 2–3 and whose sequences SEQ ID NO: 4, and SEQ ID NO: 5 represent segments. This 5.7 kb insert is cloned from the pIL105 plasmid DNA of the strain IL964 of *L. lactis ssp cremoris*, and comprises at least one gene encoding the resistance mechanism called Abi 105. SEQ ID NO: 11 is the sequence of the fragment which encodes Abi 105. The corresponding polypeptide is SEQ ID NO: 12.

DETAILED DESCRIPTION

As used in the present invention, homologous sequence is understood as meaning any sequence differing from the sequences conforming to the invention only by the substitution, deletion or addition of a small number of bases provided, naturally, that the sequence thus modified preserves the essential functional properties of the sequences of the invention.

Within this framework, two nucleotide sequences which, because of the degeneration of the genetic code, encode the same polypeptide will be considered in particular as being homologous.

The present invention also encompasses any DNA segment of more than 20 bp which can be hybridised with one of the sequences encoding Abi mechanisms such as identified above, which comprises in particular nucleic acid probes obtained from the said sequences as well as the DNA fragments of lactic acid bacteria cloned using the said probes.

The sequences SEQ ID NO: 1, SEQ ID NO: 4, SEQ ID NO: 5, SEQ ID NO: 6 have been compared with the sequence encoding the Hsp mechanism described by HILL et al. [App. Environ. Microbiol., 56, 2255–2258 (1990)]. No similarity was established between these sequences.

Moreover, no hybridisation was observed between the 9.4 kb insert encoding the Abi 420 mechanism and a 456 bp fragment derived from the gene encoding the Hsp mechanism.

The present invention furthermore relates to recombinant vectors, characterised in that they comprise at least one nucleic acid fragment such as defined above. Within this framework, the present invention encompasses in particular:

the plasmid pIL353: a sample of the strain IL3127 of *L. lactis ssp lactis* containing the said plasmid was deposited on 13 September 1990 in the Collection Nationale de Microorganismes (C.N.C.M), held by Institut Pasteur, 28, rue du Docteur Roux, 75724 Paris, under the deposition number I-999;

the plasmid pIL352: a sample of the strain IL3128 of *L. lactis ssp lactis* containing the said plasmid was deposited on 13 September 1990 in the C.N.C.M. under the deposition number I-1000;

the plasmid pIL618: a sample of the strain IL3365 of L. lactic ssp lactis containing the said plasmid was deposited on 13 September 1990 in the C.N.C.M. under the deposition number I-1001.

The invention also relates to the following polypeptides:

the polypeptide encoded by the open reading frame of the sequence SEQ ID NO: 1, and whose sequence is presented in the list of sequences under the number SEQ ID NO: 7.

the polypeptide encoded by the open reading frame ORF 2, and whose C-terminal sequence is presented in the list of sequences under the number SEQ ID NO: 8.

the polypeptide encoded by the open reading frame ORF 3, and whose sequence is presented in the list of sequences under the number SEQ ID NO: 9.

the polypeptide encoded by the open reading frame ORF 1, and whose sequence is presented in the list of sequences under the number SEQ ID NO: 10.

The present invention furthermore relates to transformed microorganisms, characterised in that they contain at least one DNA fragment conforming to the invention encoding an Abi-type mechanism of resistance to bacteriophages.

The said fragments may be carried by plasmids, or alternatively may be integrated in the bacterial chromosome by recombination or transposition.

According to a preferred embodiment of the microorganisms conforming to the invention, they contain at least two DNA fragments each encoding a different Abi mechanism.

According to another preferred embodiment of the microorganisms conforming to the invention, they contain at least three DNA fragments each encoding a different Abi mechanism.

According to a preferred feature of one or other of these embodiments, the DNA fragments encoding different Abi mechanisms are carried by the same vector.

According to another preferred feature of one or other of these embodiments, the DNA fragments encoding different Abi mechanisms are carried by different vectors.

The invention will be better understood with the help of the following additional description which refers to examples of production of DNA fragments, recombinant plasmids, and transformed microorganisms conforming to the invention.

It goes without saying however that these examples and the corresponding descriptive sections are given solely as illustration of the subject of the invention and do not constitute in any manner a limitation thereof.

EXAMPLE 1

Cloning of a DNA Fragment Encoding the Mechanism of Resistance to the Phages Abi 416

The manipulation of DNA, the cloning and the transformation of bacterial cells are, in the absence of indications to the contrary, carried out according to the procedures described by MANIATIS et al. [(Molecular cloning: a laboratory manual., Cold Spring Harbor Laboratory, Cold Spring Harbor N.Y. (1982)].

Sequencing of the different DNA fragments was carried out on each strand, by the dideoxynucleotide method by means of a 370A sequencer (Applied Biosystems, San Jose Calif.) using the procedure recommended by the manufacturer.

The total DNA of *L. lactis spp cremoris* IL 416 (Collection du laboratoire de Génétique Microbienne, Institut National de la Recherche Agronomique—78350 JOUY EN JOSAS) is partially digested by the endonuclease Sau3A and the fragments of an average size of about 10 kb are ligated at the BamHI site of the plasmid pIL253 carrying an erythromycin resistance gene. The plasmids pIL253 and pIL252 have been described by SIMON and CHOPIN, [Biochimie 70, 559-566 (1988)].

The digestion of the bacterial DNA and the ligation inside the plasmid are carried out according to the procedures described by SIMON et al. [FEMS Microbiol. Lett. 26, 239-241 (1985)] and LOUREIRO DOS SANTOS and CHOPIN, [FEMS Microbiol. Lett., 42, 209-212 (1987)].

The ligation product is used to transorm bacteria belonging to the strain IL1403 of *L. Lactic ssp lactis*, which is a strain lacking plasmids [CHOPIN et al., Plasmid, 11, 260-263 (1984)], by protoplast fusion according to the technique described by SIMON et al., [Appl. Environ. Microbiol., 52, 394-395 (1986)]. The erythromycin-resistant bacteria are then selected on the basis of their resistance to phages; colonies contained in an agar medium are dispersed in a salt solution by means of an ULTRA-TURAX T18/20 mixer (20,000 rpm) and 2 ml of the suspension are used to inoculate 100 ml of M17 medium [TERZAGHI and SANDINE, Appl. Microbiol. 29, 807–813 (1975)] in which lactose is replaced by glucose (M17glc), and containing 5 µg/ml of erythromycin. After incubating overnight at 30° C., 100 µl of various dilutions of the culture are mixed with 50 µl of 0.1M $CaCl_2$ and $10^7$ phage particles.

After 5 min at room temperature, 3 ml of M17glc agar medium containing erythromycin are added and the mixture is poured on the surface of an M17glc agar +erythromycin solid culture medium. Control cultures are carried out by culturing the IL1403 strain in the absence of erythromycin.

The phage-resistant colonies are cloned.

Under these conditions, a clone resistant to phage attack and containing a recombinant plasmid carrying an insert of about 5 kb was cloned. This recombinant plasmid was called pIL353. A sample of the strain IL3127 of *L. lactis ssp lactis* containing the said plasmid was deposited on 13 September 1990 in the Collection Nationale de Microorganismes (C.N.C.M), held by Institut Pasteur, 28, rue du Docteur Roux, 75724 Paris, under the deposition number I-999.

FIG. 1 shows the restriction map of the pIL353 plasmid. The distances between the restriction sites are indicated in kb.

A 2.1 kb fragment SphI-EcoRI, containing all the sequence encoding the Abi 416 mechanism was subcloned from the plasmid pIL353. This fragment was sequenced and the gene encoding the Abi 416 mechanism was identified.

The gene sequence is indicated in the list of sequences under the number SEQ ID NO: 1.

Sequencing of the 2.1 kb insert has also revealed the presence in the latter, immediately upstream of the structural gene of the Abi 416 mechanism, of a ISS1-type insertion sequence; the promoter sequences of the Abi 416 gene are situated in this insertion sequence.

EXAMPLE 2

Cloning of a 9.5 kb Fragment of the Total DNA of the Strain IL420 of *L. lactis ssp lactis* Encoding the Abi 420 Mechanism The total DNA of *L. lactis ssp lactis* IL420 (Collection du Laboratoire de Génétique Microbienne, Institut National de la Recherche Agronomique—78350 JOUY EN JOSAS) was digested by the endonuclease Sau3A and cloned into the plasmid pIL252 [Simon and Chopin, Biochimie 70, 559-566, (1988)], according to the procedure described in Example 1.

After transformation of bacteria belonging to the strain IL1403 of *L. lactis ssp lactis*, and selection of phage-resistant bacteria as described in Example 1, a clone containing an insert of about 9.4 kb was isolated.

Figure 2:
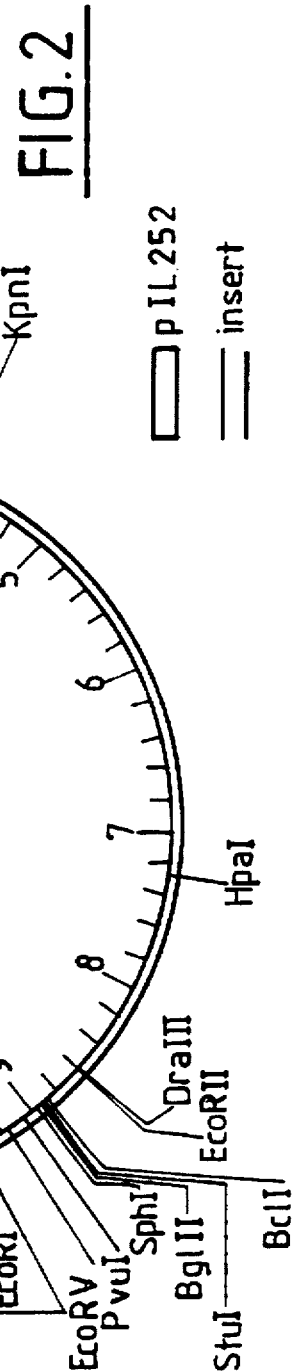
FIG. 2 shows a restriction map of the recombinant plasmid pIL352.

This insert is carried by the recombinant plasmid pIL352, whose restriction map is shown in FIG. 2. A sample of the strain IL3128 of *L. lactis ssp lactis* containing the said plasmid was deposited on 13 September 1990 in the C.N.C.M. under the deposition number I-1000.

Hybridisation experiments were carried out between the 9.4 kb insert and a fragment of 456 bp derived from the Hsp gene described by HILL et al. No hybridisation was observed, not only under stringent conditions (42° C., 50% formamide buffer), but also under non-stringent conditions (42° C., 25% formamide buffer).

EXAMPLE 3

Cloning of a DNA Fragment of the Plasmid pL105 Encoding the Abi 105 Mechanism

The plasmid pIL105 has been described by GAUTIER and CHOPIN [App. Environ. Microbiol. 53, 923–927 (1987)].

The DNA of this plasmid is digested with Sau3A and cloned into the BamHI site of piL252 according to the procedure described in Example 1.

Figure 3:
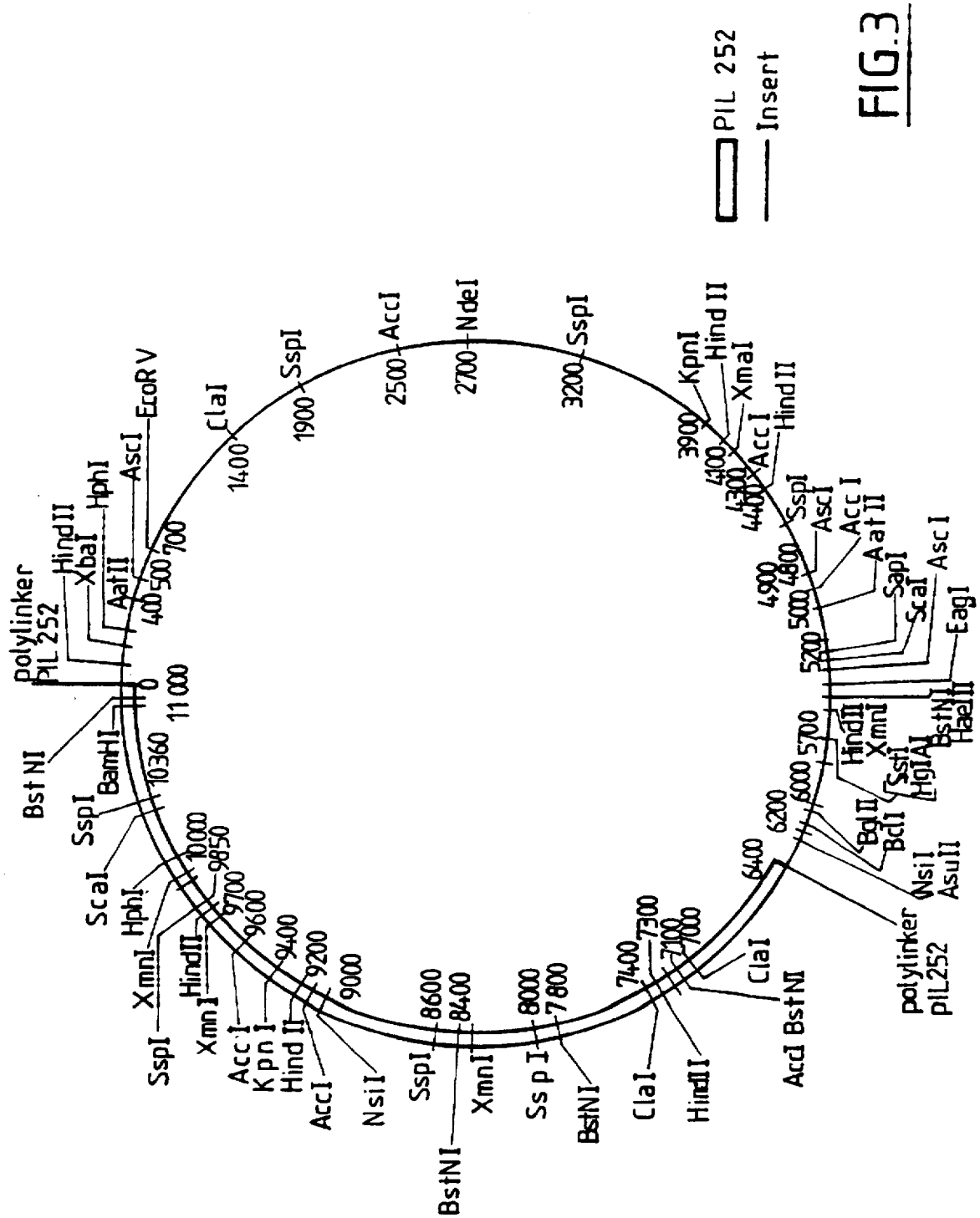
FIG. 3 shows a restriction map of the plasmid pIL305.

A recombinant plasmid carrying a 6.4 kb insert encoding the Abi 105 mechanism was selected. This plasmid was called pIL 305 and its restriction map is shown in FIG. 3.

A 700 bp fragment EcoRV-XbaI was excised from the 6.4 kb insert of pIL305; the resulting plasmid, containing a 5.7 kb insert, was called pIL618; a sample of the strain IL3365 of *L. lactis ssp lactis* containing the said plasmid was deposited on 13 September 1990 in the C.N.C.M. under the deposition number I-1001.

Figure 4:
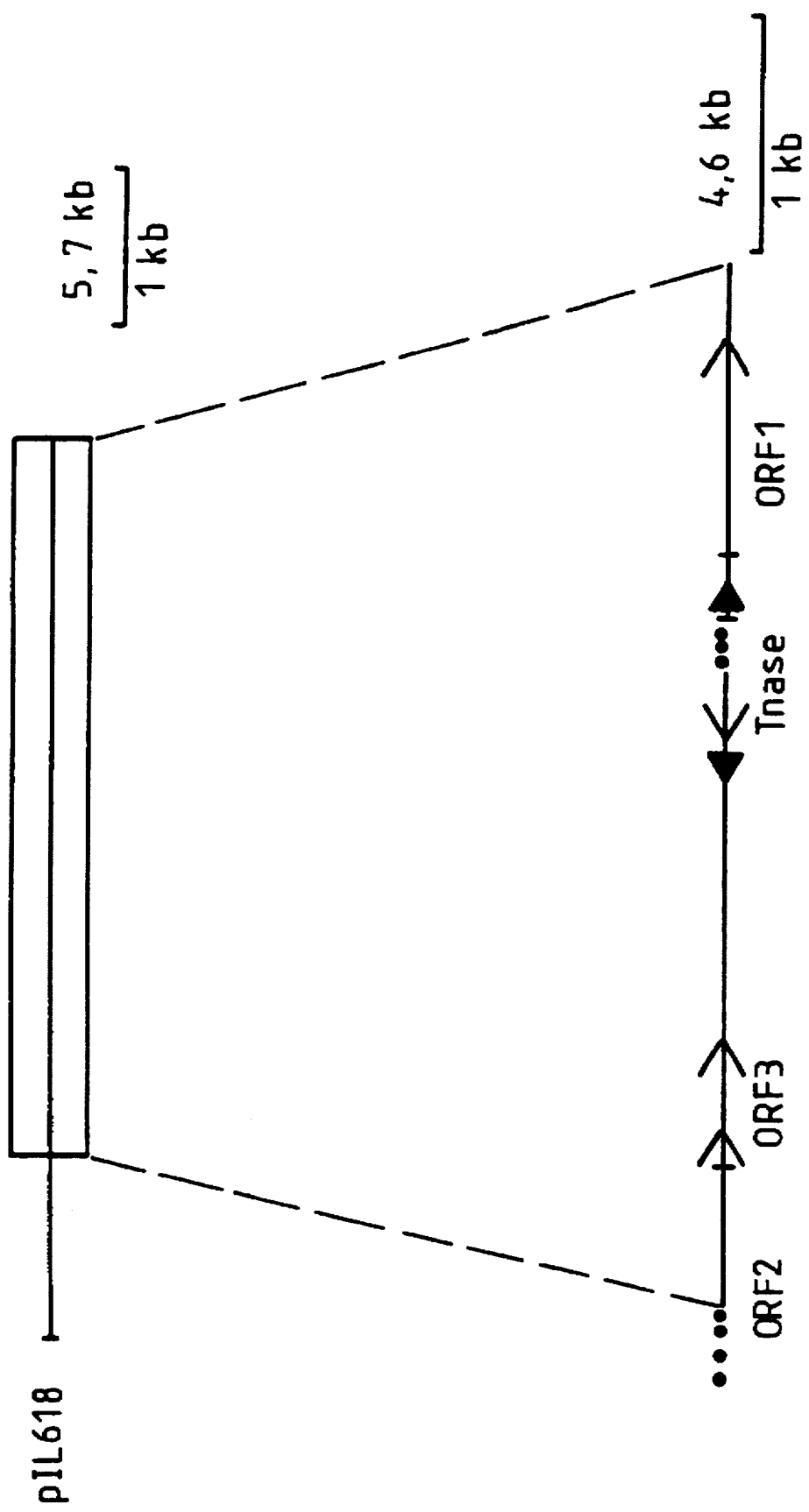
FIG. 4 shows the organization of a 5.7 kb insert contained in pIL305.

The 5.7 kb insert was partially sequenced. FIG. 4 shows the organisation of this insert: ◄►=ISS1 inverted repeat sequences; Tuase=ISS1 transposase; . . . =sequence not determined).

The sequence SEQ ID NOS: 2–3 represents about 4.6 kb of the 5.7 kb in the insert (the bases are numbered in a continuous manner without taking the nonsequenced parts into consideration). This sequence comprises 4 open reading frames.

One of them, starting from base 2289 of SEQ ID NOS: 2–3 belong to a ISS1-type insertion element and correspond to the sequence encoding the ISS1 transposase.

The other 3 open reading frames are called ORF 2, ORF 3 and ORF 1 respectively.

The partial sequence (encoding the C-terminus of the polypeptide) of ORF 2 is between bases 1 and 677 of the sequence SEQ ID NOS: 2–3. This same sequence appears separately in the list of sequences under the number SEQ ID NO: 4.

The sequence of ORF 3 is between bases 670 and 1140 of the sequence SEQ ID NOS: 2–3; it appears separately in the list of sequences under the number SEQ ID NO: 5.

The sequence of ORF 1 is between bases 3177 and 4001 of the sequence SEQ ID NOS: 2–3; it appears separately in the list of sequences under the number SEQ ID NO: 6.

II. - Resistance to Phage Attack Offered by Plasmids Carrying the DNA Sequences Abi 416, Abi 420 and Abi 105

EXAMPLE 4

Growth Experiment in a Single Step

The study was carried out using as control the strain IL1403, lacking plasmids.

The strains transformed by the plasmids pIL352 and pIL353 and pIL618 are called IL1403/pIL352 and IL403/pIL353 and IL1403/pIL618 respectively.

Adsorption experiments carried out beforehand show that the adsorption of phage particles is identical for the control strain IL1403 and for the transformed strains (of the order of 97% in 15 minutes).

A growth experiment in a single step was carried out according to the following procedure:

A culture of lactic acid bacteria in the middle of the exponential growth phase is suspended in fresh medium at a concentration of $10^7$ CFU/ml, and mixed with a suspension of phages at $10^6$ PFU/ml (phage bIL66 of the isometric type).

The mixture is incubated for 10 minutes to allow adsorption of the phages, then diluted 10-fold in the presence of antiphage serum and incubated for 5 minutes at 37° C., thus allowing about 99% of the nonadsorbed phages to be neutralised.

The mixture is then diluted again in M17 medium in order to stop the action of the antiserum and then incubated at 30° C. During this incubation, 1 ml aliquots are removed at 5-minute intervals and plated on solid medium.

The lysis plaques obtained during the lag phase give the number of infectious centres. Those obtained during the final stationary phase give the number of phages resulting from the multiplication of the phages used for the infection. The unit yield which makes it possible to evaluate the multiplication of phages is obtained by dividing the number of phages after multiplication by the number of infectious centres.

Figure 5:
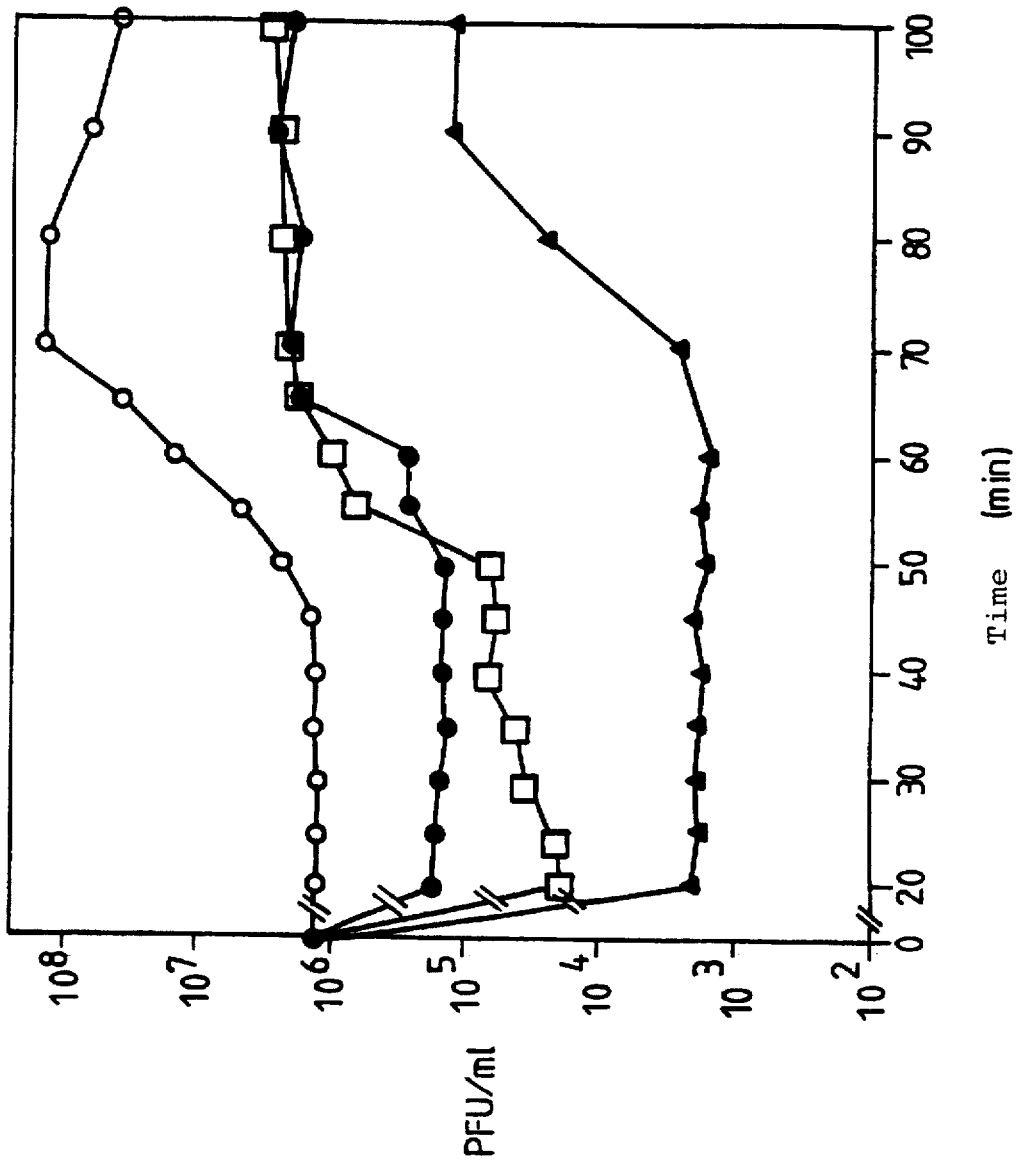
FIG. 5 shows the results of an experiment testing the resistance to phage attack offered by plasmids carrying the DNA sequences Abi 416, Abi 420 and Abi 105.

FIG. 5 shows the results of this experiment: the number of PFU per ml is represented as a function of time (in minutes), after the infection, for the strains IL1403 (○), IL1403/pIL618 (□), IL1403/pIL353 (●), IL1403/pIL352 (▲).

The lag phase is similar for all the strains. The number of infectious centres obtained for the strains IL1403/pIL352, IL1403/pIL353 and IL403/pIL618 represent 0.2%, 12% and 3% respectively of the phages adsorbed. The unit yield for the strain IL1403 is 190 and decreases to 60 for the strain IL1403/pIL352, to 25 for the strain IL1403/pIL353, and 50 for IL1403/pIL618.

The lysis plaques formed by the phage bIL66 on these transformed strains are very small, cloudy and hardly visible, as is observed for abortive viral infections. Furthermore, the phages obtained from these plaques are no longer infectious for transformed bacterial strains.

EXAMPLE 5

Comparison of the Abi 105, Abi 420 and Abi 416 Menchanisms

Different types of phages which attack lactic acid bacteria were used for this experiment: the phages bIL38, bIL66, bIL70 are of the isometric type; the phages bIL188 and bIL67 are of the elongated-head type.

Table I shows the results obtained:

TABLE I

| Plasmid | Phage | | | | |
|---|---|---|---|---|---|
| | bIL38 | bIL66 | bIL170 | bIL67 | bIL188 |
| Abi 416 | + | + | + | − | − |
| Abi 420 | + | + | − | − | − |
| Abi 105 | + | + | + | + | + |

The Abi 105 mechanism is active on the 5 phages tested whereas the Abi 416 and Abi 420 mechanisms are active only on the isometric phages. Only the Abi 416 mechanism is active on the phage bIL170.

EXAMPLE 6

Combined Effect of the Abi 105, Abi 416 and Abi 420 Mechanisms

This effect is studied by introducing the DNA fragments carrying the genes encoding these 3 mechanisms, in the bacterium IL1403.

Since the plasmids pIL252 and pIL253 are incompatible, the 5 kb insert of the plasmid pIL353 was transferred into the SalII site of the plasmid vector pGKV259 [Van der Vossen et al., Appl. Environ. Microbiol. 53, 2452–2457 (1987)], the plasmid thus obtained, called pIL377, is compatible both with the plasmid pIL105 (carrying the Abi 105 gene) and the plasmid pIL353. These plasmids are transferred separately, in pairs, or all three together, into the bacterium IL 1403.

Table II shows the results obtained.

A synergy of the efficiency of these mechanisms is moreover observed. For example, the number of plaques formed by the phage bIL 38 is divided by $10^6$ for the strain IL1403/pIL377, by $10^6$ for the strain IL1403/pIL4105 and by more than $10^8$ for the strain IL1403/pIL105/pIL 377, relative to the number of plaques formed on the strain IL1403.

Similar results are observed for the other phages in most of the combinations studied.

When the 3 Abi mechanisms are combined in the same bacterium, phage infection is practically inexis-tent. This was confirmed by a growth experiment in a single step carried out with bIL66 on the strain IL1403/pIL352/pIL105/pIL377; the number of cells infected and phages released was below the sensitivity threshold of the method.

As evident from the above, the invention is not in the least limited to the implementations, embodiments and applications which have just been described more explicitly; on the contrary, it embraces all the variants which may come to the mind of a specialist in this field without departing from the framework or the scope of the present invention.

TABLE II

| Strain | PFU/ml | | | | |
|---|---|---|---|---|---|
| | bIL38 | bIL66 | bIL170 | bIL67 | bIL188 |
| IL1403 | $3.9 \times 10^8$ | $7.7 \times 10^9$ | $6.3 \times 10^{40}$ | $6.3 \times 10^8$ | $2.7 \times 10^7$ |
| IL1403 (pIL377) | $5.0 \times 10^{2*}$ | $1.0 \times 10^{7*}$ | <10 | $1.4 \times 10^9$ | $9.6 \times 10^7$ |
| IL1403 (pIL352) | $5.0 \times 10^{3*}$ | $1.0 \times 10^{5*}$ | $1.2 \times 10^9$ | $1.5 \times 10^8$ | $1.2 \times 10^7$ |
| IL1403 (pIL105) | $5.0 \times 10^{4*}$ | $8.0 \times 10^{7*}$ | $5.0 \times 10^{3*}$ | <10 | <10 |
| IL1403 (pIL377, pIL352) | <10 | <10 | <10 | $5.7 \times 10^8$ | $5.7 \times 10^7$ |
| IL1403 (pIL377, pIL105) | <10 | $1.0 \times 10^{4*}$ | <10 | <10 | <10 |
| IL1403 (pIL352, pIL105) | <10 | $2.0 \times 10^{5*}$ | $2.0 \times 10^{*5}$ | <10 | <10 |
| IL1403 (pIL377, pIL352, | <10 | <10 | <10 | <10 | <10 |

*Cloudy plaques hardly visible.

It is claimed:

1. An isolated and purified DNA encoding a polypeptide having a sequence selected from the group consisting of SEQ ID NOS: 7, 12, 14 and 15.

2. The DNA of claim 1, having a length of about 5 kb, obtained by digesting the total DNA of IL416 with Sau3A, comprising the sequence of SEQ ID NO: 1.

3. The DNA of claim 1, having a length of about 9.4 kb, obtained by digesting pIL252 with Sau3A, comprising SEQ ID NO: 13.

4. The DNA of claim 1, having a length of about 5.7 kb, obtained by digesting pIL105 with Sau3A and excising a 0.7 kb EcoRV-XbaI fragment, comprising SEQ ID NO: 11.

5. The isolated DNA of claim 4, comprising SEQ ID NO: 2 or 3.

6. The DNA of claim 1, encoding the polypeptide of SEQ ID NO: 7.

7. A recombinant vector which comprises at least one DNA of claim 1.

8. Recombinant vector according to claim 7, characterized in that it consists of the plasmid pIL353.

9. Recombinant vector according to claim 7, characterized in that it consists of the plasmid pIL352.

10. Recombinant vector according to claim 7, characterized in that it consists of the plasmid pIL618.

11. A bacterium transformed with a hybrid vector comprising at least one DNA of claim 1, wherein said bacterium is Lactococcus or Streptococcus.

12. A bacterium of claim 11, belonging to *Lactococcus lactis ssp lactis* or *Lactococcus lactis spp cremoris*.

13. The bacterium of claim 11, transformed with a hybrid vector comprising DNA encoding at least two different polypeptides having a sequence selected from the group consisting of SEQ ID NOS: 7, 12, 14 and 15.

14. The bacterium of claim 13, transformed with a hybrid vector comprising DNA encoding at least three different polypeptides having a sequence selected from said group.

15. A process for imparting resistance to bacteriophages to a bacteria belonging to *Lactococcus lactis sp lactis* or *Lactococcus lactis sp cremoris* comprising: transforming said bacteria with the recombinant vector of claim 7.

16. An isolated DNA of more than 20 bp, comprising a fragment of SEQ ID NOS: 1, 11 or 13, wherein said isolated DNA hybridizes to a sequence complementary to said fragment.

17. An isolated DNA of more than 20 bp, comprising a fragment complementary to a sequence selected from the group consisting of SEQ ID NOS: 1, 11, and 13, wherein said isolated DNA hybridizes to said sequence.

18. The DNA of claim 17, comprising a fragment of SEQ ID NO: 1.

* * * * *

UNITED STATES PATENT AND TRADEMARK OFFICE
CERTIFICATE OF CORRECTION

PATENT NO.   : 5,629,182
DATED        : May 13, 1997
INVENTOR(S)  : Marie-Christine CHOPIN, et al.

It is certified that error appears in the above-indentified patent and that said Letters Patent is hereby corrected as shown below:

On the title page, item [73], the Assignee's name should be:

-- Institut National de la Recherche Agronomique (INRA)--

Signed and Sealed this

Sixteenth Day of September, 1997

*Attest:*

BRUCE LEHMAN

*Attesting Officer*          Commissioner of Patents and Trademarks

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 960 base pairs
        ( B ) TYPE: nucleic acid
        ( C ) STRANDEDNESS: unknown
        ( D ) TOPOLOGY: unknown ( i i ) MOLECULE TYPE: DNA (genomic)

( v i ) ORIGINAL SOURCE:
        ( A ) ORGANISM: Lactococcus cremoris
        ( B ) STRAIN: IL416

( i x ) FEATURE:
        ( A ) NAME/KEY: RBS
        ( B ) LOCATION: 80..89

( i x ) FEATURE:
        ( A ) NAME/KEY: −35_signal
        ( B ) LOCATION: 8..14

( i x ) FEATURE:
        ( A ) NAME/KEY: −10_signal
        ( B ) LOCATION: 34..38

( i x ) FEATURE:
        ( A ) NAME/KEY: terminator
        ( B ) LOCATION: 901..926

( x i ) SEQUENCE DESCRIPTION: SEQ ID NO:1:

```
TATCCTCGCT   GTCATTTTTA   TTCATTTTAC   ACTAAAATAG   ACTTATCAGA   AAACTTTGCA    60

ACAGAACCAG   AAAAAGAATA   AAAATGGAGA   TAATATGGAT   ATTGAAGTTG   ATACTTTTGA   120

GCAAGTTGAT   AGCTTTATGA   AGCAACAACA   GAAAAAAATA   GATAGTTGGC   TTTCTTTTGA   180

TAACATGCCA   ATTCCAACTG   GAATCATGAA   GCAACAAGAG   CAGAAGAAAG   TAAACACGTT   240

GAGAATGATT   TTAAAAATGT   TGCTAATTAA   TACGAGAGAT   GTATTAAATG   GCTTAATTGT   300

TTTAGAAGCT   ACGAATAACA   TGACTTCTTC   TATGATTTTG   CATAAAACCT   TGATAGAAAA   360

TACAATAAAT   ATTGGATATG   CTCTAAAATT   TTATAAAACT   AAAGATTATC   ATTCTTTTTG   420

TAATTTGATA   AAAGAAGATA   AGAAGCTTTT   TGGTAATGAA   ACAGTAAATC   AAAAAGCCAA   480

TATCTCTTTC   GTGAAATCAG   AAGGTGAAAA   ACATACACAT   ATATATCTTG   ATTATCAAGA   540

AACATGTAAA   GTAGCACATC   CTAACTTTCT   TCAATTGATA   AATTTATTAA   AAAACTACTA   600

CCCTGAATTT   TCTGAGGAGA   AATTACTAAC   ATTTGACCTT   AATGATAAAA   TATTTGGAGA   660

AGACGAAATA   AAAGTAATAC   CGATTTCAAA   ACCTAAAATA   GTCAATACGA   TTGATGAAGT   720

TATGAATGAA   ATAGCTAAAG   AAATTGTTTT   AAAATACAAT   CAGGACATGT   GTAAAGTTAC   780

ATCAAAATTA   GGAGAAATTT   CACTTACCCC   TATCCAAGAA   AAATTTGATA   AGCTAAAAGA   840

CATTTGACAA   AATTAAATTA   GCATTCGGGG   TTATCACCCT   TTTTGATAAA   CTAATAAAGT   900

AGCTCATAAC   TTAACAGTTT   TGAGCTGTTT   TTGTGTATAC   TATAAATAAA   GAGTTTTCAA   960
```

( 2 ) INFORMATION FOR SEQ ID NO:2:

( i ) SEQUENCE CHARACTERISTICS:
        ( A ) LENGTH: 2763 base pairs
        ( B ) TYPE: nucleic acid
        ( C ) STRANDEDNESS: unknown
        ( D ) TOPOLOGY: unknown -continued (ii) MOLECULE TYPE: DNA (genomic)

(vi) ORIGINAL SOURCE:
    (A) ORGANISM: Lactococcus cremoris
    (B) STRAIN: IL964

(xi) SEQUENCE DESCRIPTION: SEQ ID NO:2:

| | | | | | |
|---|---|---|---|---|---|
| AGTATTCGAT | TATTTGTAT | CGTTGGTTAT | CCATGAATTA | TAACCAATAC | GAACATTACA | 60 |
| GCGTGAAAGG | GGGACGGAGA | GCCGACCAAG | TGGAAGCCTA | CCGCCCCCCC | TCAATAAAAG | 120 |
| TGAAAGAATT | GCGAGAAATA | ACTGATACAA | TAAATGAACA | TCAACATTTC | CCCCATTTTG | 180 |
| AAACTAGAGT | ATTAAAAAAA | GCAATTGAAG | AAATCAACGC | TCACACCTCT | TTTAATGTGA | 240 |
| CCTATGAGAA | AGTCAAAAAA | GGGCGTTCAA | TTGATTCTAT | TGTCTTTCAT | ATTGAGAAGA | 300 |
| AACGCTTGGC | AGACGATAAC | AGCTACAAGT | TGGAAGATAA | AGTCTACCAA | GAAGATAAAG | 360 |
| CACGTAAAGC | AGAAACAGAA | AAAGACCTTG | TTTTCCAAGC | TATGCAAAGC | CCTTATACAC | 420 |
| GGCTGTTGAT | TGAAAATATG | TTTTTAAATG | TTTATGAAAC | AACGGACAGT | CAAATAATGG | 480 |
| CAGGCTTACA | GAAAAACGTT | TATCCACTTT | ATGACGAGTT | AAAGGAATTA | AGAGGGCTAA | 540 |
| ATGGTGTCAA | AGACCACTTG | TCTTATGTAT | CTAGCAAACA | AGAAGCCTAT | TCTAAACGCA | 600 |
| ATGTAGCGAA | GTATTTGAAG | AAAGCCATTG | AACAATACCT | ACCAACCGTT | AAAAGGCAGG | 660 |
| ACTTAAACCA | TGAGTGAAGA | CTTAAAAACC | ATAAAGAGT | TGGCGGACGA | GTTAGGGGTA | 720 |
| AGTAAATCAT | ATGTTGATAG | GATAATACGC | ATACTCAAAT | TGCATACTAA | ATTAGATAAA | 780 |
| GTAGGTAATA | AGTATGTAAT | TTCTAAAAAG | CAAGAAAAAT | CTATAATAAC | AAGGATTGAA | 840 |
| AATTCTAAAT | CAACAACTGA | AACGCATACT | GAATCAACAA | CTCAATCGCA | CACTAAAGTT | 900 |
| GATGCAGAAG | TTGATTTTTT | GAAAGAAGAA | ATCGCATATC | TTAAAAGTAA | TCACGATAAA | 960 |
| CAATTGACCA | ACAAGACAA | ACAGATAGAA | ACCTTAAGCA | ATCTATTAGA | CCAGCAACAG | 1020 |
| CGATTAGCTT | TGCAAGATAA | AAAGTGGCTA | GAAGAATACA | AGGCAGAAAT | AAACGACTTA | 1080 |
| AAAGCCCTAA | AAATGCCCTC | AGAGGCACGA | AAGAGGAACA | ATCAAATTAT | CGTTCACTAG | 1140 |
| AAAAAGAAAA | GGGACTTTGT | ACAAACCATA | CAAGAATCTT | ATGAATCTGA | AATCAAAGTC | 1200 |
| TTAAATCAAA | AACTAGCTGA | ACAAGAAGAA | CAAATACAGG | AGATACAAAA | AGAAAAGAA | 1260 |
| ACCAAAGAAA | AAAATGGTT | TCAGTTTTGG | AAGTGAGGTA | ATTTATGGCA | CAAACCTTTG | 1320 |
| ATAGAAAAAT | TTTAAGAGCC | TTACAAGATA | ATGGTGTAAG | AGAAATCAGA | GCTTATGAAG | 1380 |
| TCGTTTCAAA | ACGTTTGACA | ATCTTTCAAA | CAGACAGAGG | AACGTTTAAA | TATAGCGATA | 1440 |
| GTTTATATCG | GCTAGTTGCC | CCAAGACAAG | AATTATGGAG | GAATTGCACG | ACTGGTTTTA | 1500 |
| TTTCAGAAGA | AAAATACCAT | TTCTACAAAA | AATAAAATAT | CTAAGTTTGA | AAGAATAAAT | 1560 |
| AAAAGCCCTT | AAAAATGATT | TTAGGGCTTA | TTATTATTCA | AGTGGCATAA | TTCTACTCAA | 1620 |
| AACCATTTAA | AAGGGCTTAA | AAGGCAAAAT | ATGAGCTTAT | AGGACGATTC | AAGCATTAAA | 1680 |
| GGGAGTGAAA | AATTTATTTT | TCAATTTCTT | TAGTGCTTTT | TCGTTGGTTT | GCTCAACGAC | 1740 |
| AGGAGCAGTC | AGATTGAAAA | TCTGAAATAT | ATTCAAATTA | TTTTCCTAAG | GGCGCACTTA | 1800 |
| TATACCATGA | AAAATCATGG | TATAAAATGC | CAATATTTTA | GATTAAACGT | GTTGGAAAAA | 1860 |
| CTCGCTTTGC | TCATGTAAAT | AAAAACGTTA | TAAAGTATTA | TAGCGAGCTT | AGTAAGTGGA | 1920 |
| TATACACTTA | CGGTAAAAAG | GGTTCTGTTG | CGAAGTCAAA | GATTTATACG | AAAATGTCTT | 1980 |
| AAAAGAATTT | GAAATTAAGC | TCTAATTTTT | TTCAAAAAGG | GGGATTGGGG | GACACCACCA | 2040 |
| AAAATAAAAA | GATTCGTCTG | AAACGAACAA | AAATAAAATT | GGAAATTTTA | GGTTTTGTGA | 2100 |
| GTGAAAGATG | AATACTTTTT | ACTGTACTTG | GGTACCCAAG | TGCTAAGTTC | ACTAAAGACA | 2160 |

```
CTAACCCCCT ATTTTGAGCT TTCAGAGTTG ACAGATATTT GTGAGGTTGA CAAGATGAAA      2220
ATAATTCAGG TTCTGTTGCA AAGTTTAAAA ATCAAAATCA AATACAAGGT TTATAATCCT      2280
TCTTGTTCTT AAGCTAATAT TCCCATTAAG ACCTTAATCT CAGTAGATAC CGAAAATCCG      2340
AAGAGCGTTC CATTTCTCGG GTCTTTTTTG TATATTCCTC GAATTGTTTC CAATGCCCTT      2400
AATCGTGGTT GAGGCAAGTT CGTAAGACTT CGATAAAATT TATTGCGTCG TTTGATTGGT      2460
CGATGGTCTT GCTCAATGAG GTTATTGAGA TACTTCACGG TTCGATGCTC TGTCTTAGTA      2520
TATAAACCGT TACTCTGTAA CTTTCTAAAT GCAGAACCAA TAGAGGGCGC TTTATCCGTG      2580
ACAATTACTC TTGGTTGACC AAACTGTTTA TGTAGTCGTT TCAAGAACGC ATAAGCAGCT      2640
TGAGTATCCC GTTCTTGCG TAGCCAGATG TCTAAAGTCA ATCCATCCTC ATCAATTGCA      2700
CGATAGAGAT AATGCCAACG ACCTTTGATT TTGATATAAG TTTCATCCAT TTTCCACGAA      2760
TAG                                                                    2763
```

(2) INFORMATION FOR SEQ ID NO:3:

(i) SEQUENCE CHARACTERISTICS:
        (A) LENGTH: 1510 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:3:

```
TTAAAATGAT TCATTACTCT GTCCTCTCTG TCTTTTTTCT CAATTTTACA CTAAAATAGA        60
TTTTTTGGAA AACTTTGCAA CAGAACCATA AAAAGCAACA AAAACCTTAT TAAATAAGTA       120
ATTTTTCATC TTGTGTTTTT TTACAAAAT TTAAAGTTCT GGAAATTGGC TGCTTTATGG       180
ACATAAAATT TAAAAAATAA AAGGCTACTA ATTAATTATA AAAGATTCAA GAAATCAAAT       240
TAATAGATAA CATATTAATC TTAGGGTTAG CTCATTTATT GAAAATAAAC TTTTGCTCCT       300
TCTTGACATA TTTAGGATAA TATGTTTAAA TATATATATC AGTACTTGCC ACGCCTCTGC       360
TTTGTATGCG CATTATGGCC AGGCTTTTTT TTTATCATTT TGAAGGAAAA AATATGAAAA       420
ATAAACAATT ACAAAATAC AAAAGAACCT CTATGAATAT TTTTAGGACA AAATATCGTA       480
GAATTATTTC TTCAAGTCAT TATATAAAAA GAGATAAGAT TCCAAAGATA AACAATGGAC       540
TACTAATCAA AGAAGACTTA AAAGATTTTT ATTCCTTTGA AAAAATAAAA AAAAAAATTG       600
ATAAAAGTGT TCGTATTGAA GAAAGTGAGC TCGCTATTCT AAAAGAGTTT ATAGATAAGA       660
CAGGATATTT TAGATTTAGT ATCTATTTAA AGTTGATGAA GGATATTGAG GGAGTAACTG       720
TGATTGATAT TATTAAAACT TGTCAACTAG ATGGGTACAT TAGGGATAAT TTGTTTAGTT       780
TTACAACCAG ATTAGAAATG TTCTGGAAAA AAACTATCGT GGATACTATG TGTTTAAACT       840
ATGAGACTAA CGATTTTTTT CATAATATCA ATAGTCAATG TTACTTAGAT AAAAAAATAT       900
ATAAGAATGA TGAATGGGGT AATCTAATTA TTCAAGAGTT TAATAAGAGC TTTTTTTCGA       960
ATAATAGTCC AGCATTTAAG CATCATAAAA ATAAAAGGAA AAACTGTATT CCAATTTGGG      1020
CATTATTTGA GGGATTAACG TTTGGACAAA TAAATACTTT CATTACCCAA TTGGATGCAA      1080
GATATTATAA TGCTTGGGTT TCATCTATAT ATAATAATCC TGCATATAAA AAGCCTATGA      1140
AAAGCTGGAT AACCGTAATA CGTACATCAA GAAATAGATC TGCACATAAT TCAAGAATTT      1200
ATGGTTTGAA AGCACCCGAT GTTCCTATGG ATTTTTAAAA AAGACATCAC GGTAACTATT      1260
TTTCTGATAA CAAATCAAAA AATATAGATT CTACTTTGTT ATTTGGAACT CTTTATGTCA      1320
```

-continued

```
TTAAGCACTT ATTCATGTAT GAGAATGATC ATATAAAAGA GAATTGGAAT AATTTTATTT      1380

ATAAACTCAA TGATAAACTA TTAGAAATAA AAAAAATAGA AAAAAGTCAG TATGGTTTTT      1440

CTGAGGATTG GGTTAAACAG TTAGAAATAA TAGATTAAAT TTTAAGGAGC AATAGTCTCC      1500

CTTTTAGTGT                                                             1510
```

( 2 ) INFORMATION FOR SEQ ID NO:4:

( i ) SEQUENCE CHARACTERISTICS:
        ( A ) LENGTH: 677 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:4:

```
AGTATTCGAT TATTTGTAT  CGTTGGTTAT CCATGAATTA TAACCAATAC GAACATTACA       60

GCGTGAAAGG GGGACGGAGA GCCGACCAAG TGGAAGCCTA CCGCCCCCCC TCAATAAAAG      120

TGAAAGAATT GCGAGAAATA ACTGATACAA TAAATGAACA TCAACATTTC CCCCATTTTG      180

AAACTAGAGT ATTAAAAAAA GCAATTGAAG AAATCAACGC TCACACCTCT TTTAATGTGA      240

CCTATGAGAA AGTCAAAAAA GGGCGTTCAA TTGATTCTAT TGTCTTTCAT ATTGAGAAGA      300

AACGCTTGGC AGACGATAAC AGCTACAAGT TGGAAGATAA AGTCTACCAA GAAGATAAAG      360

CACGTAAAGC AGAAACAGAA AAAGACCTTG TTTTCCAAGC TATGCAAAGC CCTTATACAC      420

GGCTGTTGAT TGAAAATATG TTTTTAAATG TTTATGAAAC AACGGACAGT CAAATAATGG      480

CAGGCTTACA GAAAAACGTT TATCCACTTT ATGACGAGTT AAAGGAATTA AGAGGGCTAA      540

ATGGTGTCAA AGACCACTTG TCTTATGTAT CTAGCAAACA AGAAGCCTAT TCTAAACGCA      600

ATGTAGCGAA GTATTTGAAG AAAGCCATTG AACAATACCT ACCAACCGTT AAAAGGCAGG      660

ACTTAAACCA TGAGTGA                                                    677
```

( 2 ) INFORMATION FOR SEQ ID NO:5:

( i ) SEQUENCE CHARACTERISTICS:
        ( A ) LENGTH: 471 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:5:

```
ATGAGTGAAG ACTTAAAAAC CATAAAAGAG TTGGCGGACG AGTTAGGGGT AAGTAAATCA       60

TATGTTGATA GGATAATACG CATACTCAAA TTGCATACTA AATTAGATAA AGTAGGTAAT      120

AAGTATGTAA TTTCTAAAAA GCAAGAAAAA TCTATAATAA CAAGGATTGA AAATTCTAAA      180

TCAACAACTG AAACGCATAC TGAATCAACA ACTCAATCGC ACACTAAAGT TGATGCAGAA      240

GTTGATTTTT TGAAAGAAGA AATCGCATAT CTTAAAAGTA ATCACGATAA ACAATTGACC      300

AACAAAGACA AACAGATAGA AACCTTAAGC AATCTATTAG ACCAGCAACA GCGATTAGCT      360

TTGCAAGATA AAAAGTGGCT AGAAGAATAC AAGGCAGAAA TAAACGACTT AAAAGCCCTA      420

AAAATGCCCT CAGAGGCACG AAAGAGGAAC AATCAAATTA TCGTTCACTA G               471
```

( 2 ) INFORMATION FOR SEQ ID NO:6:

( i ) SEQUENCE CHARACTERISTICS:
        ( A ) LENGTH: 1240 base pairs
        ( B ) TYPE: nucleic acid (C) STRANDEDNESS: unknown
(D) TOPOLOGY: unknown (i i) MOLECULE TYPE: DNA (genomic)

(i x) FEATURE:
(A) NAME/KEY: -35_signal
(B) LOCATION: 33..38

(i x) FEATURE:
(A) NAME/KEY: -10_signal
(B) LOCATION: 57..62

(i x) FEATURE:
(A) NAME/KEY: RBS
(B) LOCATION: 133..137

(x i) SEQUENCE DESCRIPTION: SEQ ID NO:6:

| | | | | | |
|---|---|---|---|---|---|
| CTCATTTATT | GAAAATAAAC | TTTTGCTCCT | TCTTGACATA | TTTAGGATAA | TATGTTTAAA | 60 |
| TATATATATC | AGTACTTGCC | ACGCCTCTGC | TTTGTATGCG | CATTATGGCC | AGGCTTTTT | 120 |
| TTTATCATTT | TGAAGGAAAA | AATATGAAAA | ATAAACAATT | ACAAAAATAC | AAAAGAACCT | 180 |
| CTATGAATAT | TTTAGGACA | AAATATCGTA | GAATTATTTC | TTCAAGTCAT | TATATAAAA | 240 |
| GAGATAAGAT | TCCAAAGATA | AACAATGGAC | TACTAATCAA | AGAAGACTTA | AAAGATTTTT | 300 |
| ATTCCTTTGA | AAAAATAAAA | AAAAAAATTG | ATAAAGTGT | TCGTATTGAA | GAAAGTGAGC | 360 |
| TCGCTATTCT | AAAAGAGTTT | ATAGATAAGA | CAGGATATTT | TAGATTAGT | ATCTATTAA | 420 |
| AGTTGATGAA | GGATATTGAG | GGAGTAACTG | TGATTGATAT | TATTAAAACT | TGTCAACTAG | 480 |
| ATGGGTACAT | TAGGGATAAT | TTGTTTAGTT | TTACAACCAG | ATTAGAAATG | TTCTGGAAAA | 540 |
| AAACTATCGT | GGATACTATG | TGTTTAAACT | ATGAGACTAA | CGATTTTTT | CATAATATCA | 600 |
| ATAGTCAATG | TTACTTAGAT | AAAAAATAT | ATAAGAATGA | TGAATGGGGT | AATCTAATTA | 660 |
| TTCAAGAGTT | TAATAAGAGC | TTTTTTTCGA | ATAATAGTCC | AGCATTTAAG | CATCATAAAA | 720 |
| ATAAAAGGAA | AAACTGTATT | CCAATTTGGG | CATTATTTGA | GGGATTAACG | TTTGGACAAA | 780 |
| TAAATACTTT | CATTACCCAA | TTGGATGCAA | GATATTATAA | TGCTTGGGTT | TCATCTATAT | 840 |
| ATAATAATCC | TGCATATAAA | AAGCCTATGA | AAAGCTGGAT | AACCGTAATA | CGTACATCAA | 900 |
| GAAATAGATC | TGCACATAAT | TCAAGAATTT | ATGGTTTGAA | AGCACCCGAT | GTTCCTATGG | 960 |
| ATTTTAAAA | AAGACATCAC | GGTAACTATT | TTCTGATAA | CAAATCAAAA | AATATAGATT | 1020 |
| CTACTTTGTT | ATTTGGAACT | CTTTATGTCA | TTAAGCACTT | ATTCATGTAT | GAGAATGATC | 1080 |
| ATATAAAAGA | GAATTGGAAT | AATTTATTT | ATAAACTCAA | TGATAAACTA | TTAGAAATAA | 1140 |
| AAAAAATAGA | AAAAAGTCAG | TATGGTTTTT | CTGAGGATTG | GGTTAAACAG | TTAGAAATAA | 1200 |
| TAGATTAAAT | TTTAAGGAGC | AATAGTCTCC | CTTTTAGTGT | | | 1240 |

(2) INFORMATION FOR SEQ ID NO:7:

(i) SEQUENCE CHARACTERISTICS:
(A) LENGTH: 250 amino acids
(B) TYPE: amino acid
(D) TOPOLOGY: unknown (i i) MOLECULE TYPE: protein (x i) SEQUENCE DESCRIPTION: SEQ ID NO:7:

```
Met  Asp  Ile  Glu  Val  Asp  Thr  Phe  Glu  Gln  Val  Asp  Ser  Phe  Met  Lys
 1                  5                   10                      15

Gln  Gln  Gln  Lys  Lys  Ile  Asp  Ser  Trp  Leu  Ser  Phe  Asp  Asn  Met  Pro
                20                  25                      30

Ile  Pro  Thr  Gly  Ile  Met  Lys  Gln  Gln  Glu  Gln  Lys  Lys  Val  Asn  Thr
```

|       |       |       |       | 35    |       |       |       | 40    |       |       |       | 45    |       |       |
| ----- | ----- | ----- | ----- | ----- | ----- | ----- | ----- | ----- | ----- | ----- | ----- | ----- | ----- | ----- |

Leu Arg Met Ile Leu Lys Met Leu Leu Ile Asn Thr Arg Asp Val Leu
            50                  55                  60
Asn Gly Leu Ile Val Leu Glu Ala Thr Asn Asn Met Thr Ser Ser Met
 65                  70                  75                  80
Ile Leu His Lys Thr Leu Ile Glu Asn Thr Ile Asn Ile Gly Tyr Ala
                 85                  90                  95
Leu Lys Phe Tyr Lys Thr Lys Asp Tyr His Ser Phe Cys Asn Leu Ile
                100                 105                 110
Lys Glu Asp Lys Lys Leu Phe Gly Asn Glu Thr Val Asn Gln Lys Ala
            115                 120                 125
Asn Ile Ser Phe Val Lys Ser Glu Gly Glu Lys His Thr His Ile Tyr
    130                 135                 140
Leu Asp Tyr Gln Glu Thr Cys Lys Val Ala His Pro Asn Phe Leu Gln
145                 150                 155                 160
Leu Ile Asn Leu Leu Lys Asn Tyr Tyr Pro Glu Phe Ser Glu Glu Lys
                165                 170                 175
Leu Leu Thr Phe Asp Leu Asn Asp Lys Ile Phe Gly Glu Asp Glu Ile
            180                 185                 190
Lys Val Ile Pro Ile Ser Lys Pro Lys Ile Val Asn Thr Ile Asp Glu
        195                 200                 205
Val Met Asn Glu Ile Ala Lys Glu Ile Val Leu Lys Tyr Asn Gln Asp
    210                 215                 220
Met Cys Lys Val Thr Ser Lys Leu Gly Glu Ile Ser Leu Thr Pro Ile
225                 230                 235                 240
Gln Glu Lys Phe Asp Lys Leu Lys Asp Ile
            245                 250

( 2 ) INFORMATION FOR SEQ ID NO:8:

( i ) SEQUENCE CHARACTERISTICS:
        ( A ) LENGTH: 224 amino acids
        ( B ) TYPE: amino acid
        ( D ) TOPOLOGY: unknown ( i i ) MOLECULE TYPE: protein ( x i ) SEQUENCE DESCRIPTION: SEQ ID NO:8:

Tyr Ser Ile Ile Leu Tyr Arg Trp Leu Ser Met Asn Tyr Asn Gln Tyr
 1               5                  10                  15
Glu His Tyr Ser Val Lys Gly Gly Arg Arg Ala Asp Gln Val Glu Ala
             20                  25                  30
Tyr Arg Pro Pro Ser Ile Lys Val Lys Glu Leu Arg Glu Ile Thr Asp
         35                  40                  45
Thr Ile Asn Glu His Gln His Phe Pro His Phe Glu Thr Arg Val Leu
     50                  55                  60
Lys Lys Ala Ile Glu Glu Ile Asn Ala His Thr Ser Phe Asn Val Thr
 65                  70                  75                  80
Tyr Glu Lys Val Lys Lys Gly Arg Ser Ile Asp Ser Ile Val Phe His
                 85                  90                  95
Ile Glu Lys Lys Arg Leu Ala Asp Asp Asn Ser Tyr Lys Leu Glu Asp
                100                 105                 110
Lys Val Tyr Gln Glu Asp Lys Ala Arg Lys Ala Glu Thr Glu Lys Asp
            115                 120                 125
Leu Val Phe Gln Ala Met Gln Ser Pro Tyr Thr Arg Leu Leu Ile Glu
    130                 135                 140

```
Asn Met Phe Leu Asn Val Tyr Glu Thr Thr Asp Ser Gln Ile Met Ala
145                 150                 155                 160

Gly Leu Gln Lys Asn Val Tyr Pro Leu Tyr Asp Glu Leu Lys Glu Leu
                165             170                 175

Arg Gly Leu Asn Gly Val Lys Asp His Leu Ser Tyr Val Ser Ser Lys
            180             185             190

Gln Glu Ala Tyr Ser Lys Arg Asn Val Ala Lys Tyr Leu Lys Lys Ala
        195             200             205

Ile Glu Gln Tyr Leu Pro Thr Val Lys Arg Gln Asp Leu Asn His Glu
    210             215             220
```

(2) INFORMATION FOR SEQ ID NO:9:

(i) SEQUENCE CHARACTERISTICS:
    (A) LENGTH: 156 amino acids
    (B) TYPE: amino acid
    (D) TOPOLOGY: unknown (ii) MOLECULE TYPE: protein (xi) SEQUENCE DESCRIPTION: SEQ ID NO:9:

```
Met Ser Glu Asp Leu Lys Thr Ile Lys Glu Leu Ala Asp Glu Leu Gly
1               5                   10                  15

Val Ser Lys Ser Tyr Val Asp Arg Ile Ile Arg Ile Leu Lys Leu His
                20              25              30

Thr Lys Leu Asp Lys Val Gly Asn Lys Tyr Val Ile Ser Lys Lys Gln
            35              40              45

Glu Lys Ser Ile Ile Thr Arg Ile Glu Asn Ser Lys Ser Thr Thr Glu
    50              55              60

Thr His Thr Glu Ser Thr Thr Gln Ser His Thr Lys Val Asp Ala Glu
65              70              75                  80

Val Asp Phe Leu Lys Glu Ile Ala Tyr Leu Lys Ser Asn His Asp
                85              90              95

Lys Gln Leu Thr Asn Lys Asp Lys Gln Ile Glu Thr Leu Ser Asn Leu
            100             105             110

Leu Asp Gln Gln Gln Arg Leu Ala Leu Gln Asp Lys Lys Trp Leu Glu
        115             120             125

Glu Tyr Lys Ala Glu Ile Asn Asp Leu Lys Ala Leu Lys Met Pro Ser
    130             135             140

Glu Ala Arg Lys Arg Asn Asn Gln Ile Ile Val His
145             150             155
```

(2) INFORMATION FOR SEQ ID NO:10:

(i) SEQUENCE CHARACTERISTICS:
    (A) LENGTH: 274 amino acids
    (B) TYPE: amino acid
    (D) TOPOLOGY: unknown (ii) MOLECULE TYPE: protein (xi) SEQUENCE DESCRIPTION: SEQ ID NO:10:

```
Met Lys Asn Lys Gln Leu Gln Lys Tyr Lys Arg Thr Ser Met Asn Ile
1               5                   10                  15

Phe Arg Thr Lys Tyr Arg Arg Ile Ile Ser Ser Ser His Tyr Ile Lys
                20              25              30

Arg Asp Lys Ile Pro Lys Ile Asn Asn Gly Leu Leu Ile Lys Glu Asp
            35              40              45

Leu Lys Asp Phe Tyr Ser Phe Glu Lys Ile Lys Lys Ile Asp Lys
        50              55              60
```

```
Ser  Val  Arg  Ile  Glu  Glu  Ser  Glu  Leu  Ala  Ile  Leu  Lys  Glu  Phe  Ile
65              70                       75                        80

Asp  Lys  Thr  Gly  Tyr  Phe  Arg  Phe  Ser  Ile  Tyr  Leu  Lys  Leu  Met  Lys
                85                       90                        95

Asp  Ile  Glu  Gly  Val  Thr  Val  Ile  Asp  Ile  Ile  Lys  Thr  Cys  Gln  Leu
               100                      105                  110

Asp  Gly  Tyr  Ile  Arg  Asp  Asn  Leu  Phe  Ser  Phe  Thr  Thr  Arg  Leu  Glu
               115                 120                       125

Met  Phe  Trp  Lys  Lys  Thr  Ile  Val  Asp  Thr  Met  Cys  Leu  Asn  Tyr  Glu
     130                      135                  140

Thr  Asn  Asp  Phe  Phe  His  Asn  Ile  Asn  Ser  Gln  Cys  Tyr  Leu  Asp  Lys
145                      150                      155                        160

Lys  Ile  Tyr  Lys  Asn  Asp  Glu  Trp  Gly  Asn  Leu  Ile  Ile  Gln  Glu  Phe
                165                      170                       175

Asn  Lys  Ser  Phe  Phe  Ser  Asn  Asn  Ser  Pro  Ala  Phe  Lys  His  His  Lys
                180                 185                       190

Asn  Lys  Arg  Lys  Asn  Cys  Ile  Pro  Ile  Trp  Ala  Leu  Phe  Glu  Gly  Leu
          195                      200                       205

Thr  Phe  Gly  Gln  Ile  Asn  Thr  Phe  Ile  Thr  Gln  Leu  Asp  Ala  Arg  Tyr
     210                      215                  220

Tyr  Asn  Ala  Trp  Val  Ser  Ser  Ile  Tyr  Asn  Asn  Pro  Ala  Tyr  Lys  Lys
225                      230                 235                             240

Pro  Met  Lys  Ser  Trp  Ile  Thr  Val  Ile  Arg  Thr  Ser  Arg  Asn  Arg  Ser
                245                      250                       255

Ala  His  Asn  Ser  Arg  Ile  Tyr  Gly  Leu  Lys  Ala  Pro  Asp  Val  Pro  Met
                260                 265                       270

Asp  Phe
```

( 2 ) INFORMATION FOR SEQ ID NO: 11:

( i ) SEQUENCE CHARACTERISTICS:
        ( A ) LENGTH: 1532 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i i i ) ANTI-SENSE: NO ( v i ) ORIGINAL SOURCE:
        ( A ) ORGANISM: Lactococcus lactis
        ( B ) STRAIN: IL964

( i x ) FEATURE:
        ( A ) NAME/KEY: -35_signal
        ( B ) LOCATION: 308..314

( i x ) FEATURE:
        ( A ) NAME/KEY: -10_signal
        ( B ) LOCATION: 331..336

( i x ) FEATURE:
        ( A ) NAME/KEY: RBS
        ( B ) LOCATION: 408..412

( i x ) FEATURE:
        ( A ) NAME/KEY: CDS
        ( B ) LOCATION: 419..1471

( x i ) SEQUENCE DESCRIPTION: SEQ ID NO: 11:

```
ATCTTTTAAA  ATGATTCATT  ACTCTGTCCT  CTCTGTCTTT  TTTCTCAATT  TTACACTAAA          60
```

```
ATAGATTTTT TGGAAAACTT TGCAACAGAA CCATAAAAAG CAACAAAAAC CTTATTAAAT        120

AAGTAATTTT TCATCTTGTG TTTTTTTAC  AAAATTTAAA GTTCTGGAAA TTGGCTGCTT        180

TATGGACATA AAATTTAAAA AATAAAAGGC TACTAATTAA TTATAAAAGA TTCAAGAAAT        240

CAAATTAATA GATAACATAT TAATCTTAGG GTTAGCTCAT TTATTGAAAA TAAACTTTTG        300

CTCCTTCTTG ACATATTTAG GATAATATGT TTAAATATAT ATATCAGTAC TTGCCACGCC        360

TCTGCTTTGT ATGCGCATTA TGGCCAGGCT TTTTTTTAT  CATTTGAAG  GAAAAAT          418
```

| | | | | | | | | | | | | | | | | |
|---|---|---|---|---|---|---|---|---|---|---|---|---|---|---|---|---|
| ATG | AAA | AAT | AAA | CAA | TTA | CAA | AAA | TAC | AAA | AGA | ACC | TCT | ATG | AAT | ATT | 466 |
| Met | Lys | Asn | Lys | Gln | Leu | Gln | Lys | Tyr | Lys | Arg | Thr | Ser | Met | Asn | Ile | |
| 1 | | | | 5 | | | | | 10 | | | | | 15 | | |
| TTT | AGG | ACA | AAA | TAT | CGT | AGA | ATT | ATT | TCT | TCA | AGT | CAT | TAT | ATA | AAA | 514 |
| Phe | Arg | Thr | Lys | Tyr | Arg | Arg | Ile | Ile | Ser | Ser | Ser | His | Tyr | Ile | Lys | |
| | | | 20 | | | | | 25 | | | | | 30 | | | |
| AGA | GAT | AAG | ATT | CCA | AAG | ATA | AAC | AAT | GGA | CTA | CTA | ATC | AAA | GAA | GAC | 562 |
| Arg | Asp | Lys | Ile | Pro | Lys | Ile | Asn | Asn | Gly | Leu | Leu | Ile | Lys | Glu | Asp | |
| | | 35 | | | | | 40 | | | | | 45 | | | | |
| TTA | AAA | GAT | TTT | TAT | TCC | TTT | GAA | AAA | ATA | AAA | AAA | AAA | ATT | GAT | AAA | 610 |
| Leu | Lys | Asp | Phe | Tyr | Ser | Phe | Glu | Lys | Ile | Lys | Lys | Lys | Ile | Asp | Lys | |
| | 50 | | | | | 55 | | | | | 60 | | | | | |
| AGT | GTT | CGT | ATT | GAA | GAA | AGT | GAG | CTC | GCT | ATT | CTA | AAA | GAG | TTT | ATA | 658 |
| Ser | Val | Arg | Ile | Glu | Glu | Ser | Glu | Leu | Ala | Ile | Leu | Lys | Glu | Phe | Ile | |
| 65 | | | | | 70 | | | | | 75 | | | | | 80 | |
| GAT | AAG | ACA | GGA | TAT | TTT | AGA | TTT | AGT | ATC | TAT | TTA | AAG | TTG | ATG | AAG | 706 |
| Asp | Lys | Thr | Gly | Tyr | Phe | Arg | Phe | Ser | Ile | Tyr | Leu | Lys | Leu | Met | Lys | |
| | | | | 85 | | | | | 90 | | | | | 95 | | |
| GAT | ATT | GAG | GGA | GTA | ACT | GTG | ATT | GAT | ATT | ATT | AAA | ACT | TGT | CAA | CTA | 754 |
| Asp | Ile | Glu | Gly | Val | Thr | Val | Ile | Asp | Ile | Ile | Lys | Thr | Cys | Gln | Leu | |
| | | | 100 | | | | | 105 | | | | | 110 | | | |
| GAT | GGG | TAC | ATT | AGG | GAT | AAT | TTG | TTT | AGT | TTT | ACA | ACC | AGA | TTA | GAA | 802 |
| Asp | Gly | Tyr | Ile | Arg | Asp | Asn | Leu | Phe | Ser | Phe | Thr | Thr | Arg | Leu | Glu | |
| | | 115 | | | | | 120 | | | | | 125 | | | | |
| ATG | TTC | TGG | AAA | AAA | ACT | ATC | GTG | GAT | ACT | ATG | TGT | TTA | AAC | TAT | GAG | 850 |
| Met | Phe | Trp | Lys | Lys | Thr | Ile | Val | Asp | Thr | Met | Cys | Leu | Asn | Tyr | Glu | |
| | 130 | | | | | 135 | | | | | 140 | | | | | |
| ACT | AAC | GAT | TTT | TTT | CAT | AAT | AGT | CAA | TGT | TAC | TTA | GAT | AAA | AAA | ATA | 898 |
| Thr | Asn | Asp | Phe | Phe | His | Asn | Ser | Gln | Cys | Tyr | Leu | Asp | Lys | Lys | Ile | |
| 145 | | | | | 150 | | | | | 155 | | | | | 160 | |
| TAT | AAG | AAT | GAT | GAA | TGG | GGT | AAT | CTA | ATT | ATT | CAA | GAG | TTT | AAT | AAG | 946 |
| Tyr | Lys | Asn | Asp | Glu | Trp | Gly | Asn | Leu | Ile | Ile | Gln | Glu | Phe | Asn | Lys | |
| | | | | 165 | | | | | 170 | | | | | 175 | | |
| AGC | TTT | TTT | TCG | AAT | AAT | AGT | CCA | GCA | TTT | AAG | CAT | CAT | AAA | AAT | AAA | 994 |
| Ser | Phe | Phe | Ser | Asn | Asn | Ser | Pro | Ala | Phe | Lys | His | His | Lys | Asn | Lys | |
| | | | 180 | | | | | 185 | | | | | 190 | | | |
| AAG | AAA | AAC | TGT | ATT | CCA | ATT | TGG | GCA | TTA | TTT | GAG | GGA | TTA | ACG | TTT | 1042 |
| Lys | Lys | Asn | Cys | Ile | Pro | Ile | Trp | Ala | Leu | Phe | Glu | Gly | Leu | Thr | Phe | |
| | | 195 | | | | | 200 | | | | | 205 | | | | |
| GGA | CAA | ATA | AAT | ACT | TTC | ATT | ACC | CAA | TTG | GAT | GCA | AGA | TAT | TAT | AAT | 1090 |
| Gly | Gln | Ile | Asn | Thr | Phe | Ile | Thr | Gln | Leu | Asp | Ala | Arg | Tyr | Tyr | Asn | |
| | 210 | | | | | 215 | | | | | 220 | | | | | |
| GCT | TGG | GTT | TCA | TCT | ATA | TAT | AAT | AAT | CCT | GCA | TAT | AAA | AAG | CCT | ATG | 1138 |
| Ala | Trp | Val | Ser | Ser | Ile | Tyr | Asn | Asn | Pro | Ala | Tyr | Lys | Lys | Pro | Met | |
| 225 | | | | | 230 | | | | | 235 | | | | | 240 | |
| AAA | AGC | TGG | ATA | ACC | GTA | ATA | CGT | ACA | TCA | AGA | AAT | AGA | TCT | GCA | CAT | 1186 |
| Lys | Ser | Trp | Ile | Thr | Val | Ile | Arg | Thr | Ser | Arg | Asn | Arg | Ser | Ala | His | |
| | | | | 245 | | | | | 250 | | | | | 255 | | |
| AAT | TCA | AGA | GTT | TAT | GGT | TTG | AAA | GCA | ACC | GAT | GTT | CCT | ATG | ATT | TTA | 1234 |
| Asn | Ser | Arg | Val | Tyr | Gly | Leu | Lys | Ala | Thr | Asp | Val | Pro | Met | Ile | Leu | |
| | | | 260 | | | | | 265 | | | | | 270 | | | |

| | | | | | | | | | | | | | | | | |
|---|---|---|---|---|---|---|---|---|---|---|---|---|---|---|---|---|
| AAA | AAG | CAT | CAC | GTA | ACT | ATT | TTC | TTG | GAT | AAC | AAA | TCA | AAA | AAT | ATA | 1282 |
| Lys | Lys | His | His | Val | Thr | Ile | Phe | Leu | Asp | Asn | Lys | Ser | Lys | Asn | Ile | |
| | | 275 | | | | | 280 | | | | | 285 | | | | |
| GGT | TCT | CCT | TTG | TTA | TTT | GGA | ACT | CTT | TAT | GTC | ATT | AAG | CAC | TTA | TTC | 1330 |
| Gly | Ser | Pro | Leu | Leu | Phe | Gly | Thr | Leu | Tyr | Val | Ile | Lys | His | Leu | Phe | |
| | 290 | | | | 295 | | | | | 300 | | | | | | |
| ATG | TAT | GAG | AAT | GAT | CAT | ATA | AAA | GAG | AAT | TGG | AAT | AAT | TTT | ATT | TAT | 1378 |
| Met | Tyr | Glu | Asn | Asp | His | Ile | Lys | Glu | Asn | Trp | Asn | Asn | Phe | Ile | Tyr | |
| 305 | | | | 310 | | | | | 315 | | | | | 320 | | |
| AAA | CTC | AAT | GAT | AAA | CTA | TTA | GAA | ATA | AAA | AAA | ATA | GAA | AAA | AGT | CAG | 1426 |
| Lys | Leu | Asn | Asp | Lys | Leu | Leu | Glu | Ile | Lys | Lys | Ile | Glu | Lys | Ser | Gln | |
| | | | | 325 | | | | | 330 | | | | | 335 | | |
| TAT | GGT | TTT | TCT | GAG | GAT | TGG | GTT | AAA | CAG | TTA | GAA | ATA | ATA | GAT | | 1471 |
| Tyr | Gly | Phe | Ser | Glu | Asp | Trp | Val | Lys | Gln | Leu | Glu | Ile | Ile | Asp | | |
| | | | 340 | | | | | 345 | | | | | 350 | | | |

TAAATTTTAA GGAGCAATAG TCTCCCTTTT AGTGTGCCAA TCAAATGAAG TCATAATACT 1531

C 1532

( 2 ) INFORMATION FOR SEQ ID NO: 12:

( i ) SEQUENCE CHARACTERISTICS:
( A ) LENGTH: 351 amino acids
( B ) TYPE: amino acid
( D ) TOPOLOGY: linear ( i i ) MOLECULE TYPE: protein ( x i ) SEQUENCE DESCRIPTION: SEQ ID NO: 12:

| | | | | | | | | | | | | | | |
|---|---|---|---|---|---|---|---|---|---|---|---|---|---|---|
| Met | Lys | Asn | Lys | Gln | Leu | Gln | Lys | Tyr | Lys | Arg | Thr | Ser | Met | Asn | Ile |
| 1 | | | | 5 | | | | | 10 | | | | | 15 | |
| Phe | Arg | Thr | Lys | Tyr | Arg | Arg | Ile | Ile | Ser | Ser | Ser | His | Tyr | Ile | Lys |
| | | | 20 | | | | | 25 | | | | | 30 | | |
| Arg | Asp | Lys | Ile | Pro | Lys | Ile | Asn | Asn | Gly | Leu | Leu | Ile | Lys | Glu | Asp |
| | | 35 | | | | | 40 | | | | | 45 | | | |
| Leu | Lys | Asp | Phe | Tyr | Ser | Phe | Glu | Lys | Ile | Lys | Lys | Lys | Ile | Asp | Lys |
| | 50 | | | | | 55 | | | | | 60 | | | | |
| Ser | Val | Arg | Ile | Glu | Glu | Ser | Glu | Leu | Ala | Ile | Leu | Lys | Glu | Phe | Ile |
| 65 | | | | | 70 | | | | | 75 | | | | | 80 |
| Asp | Lys | Thr | Gly | Tyr | Phe | Arg | Phe | Ser | Ile | Tyr | Leu | Lys | Leu | Met | Lys |
| | | | | 85 | | | | | 90 | | | | | 95 | |
| Asp | Ile | Glu | Gly | Val | Thr | Val | Ile | Asp | Ile | Ile | Lys | Thr | Cys | Gln | Leu |
| | | | 100 | | | | | 105 | | | | | 110 | | |
| Asp | Gly | Tyr | Ile | Arg | Asp | Asn | Leu | Phe | Ser | Phe | Thr | Thr | Arg | Leu | Glu |
| | | 115 | | | | | 120 | | | | | 125 | | | |
| Met | Phe | Trp | Lys | Lys | Thr | Ile | Val | Asp | Thr | Met | Cys | Leu | Asn | Tyr | Glu |
| | 130 | | | | | 135 | | | | | 140 | | | | |
| Thr | Asn | Asp | Phe | Phe | His | Asn | Ser | Gln | Cys | Tyr | Leu | Asp | Lys | Lys | Ile |
| 145 | | | | | 150 | | | | | 155 | | | | | 160 |
| Tyr | Lys | Asn | Asp | Glu | Trp | Gly | Asn | Leu | Ile | Ile | Gln | Glu | Phe | Asn | Lys |
| | | | | 165 | | | | | 170 | | | | | 175 | |
| Ser | Phe | Phe | Ser | Asn | Asn | Ser | Pro | Ala | Phe | Lys | His | His | Lys | Asn | Lys |
| | | | 180 | | | | | 185 | | | | | 190 | | |
| Lys | Lys | Asn | Cys | Ile | Pro | Ile | Trp | Ala | Leu | Phe | Glu | Gly | Leu | Thr | Phe |
| | | 195 | | | | | 200 | | | | | 205 | | | |
| Gly | Gln | Ile | Asn | Thr | Phe | Ile | Thr | Gln | Leu | Asp | Ala | Arg | Tyr | Tyr | Asn |
| | 210 | | | | | 215 | | | | | 220 | | | | |
| Ala | Trp | Val | Ser | Ser | Ile | Tyr | Asn | Asn | Pro | Ala | Tyr | Lys | Lys | Pro | Met |

|     |     |     |     |     |     |     |     |     |     |     |     |     |     |     |     |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |
| Lys | Ser | Trp | Ile | Thr | Val | Ile | Arg | Thr | Ser | Arg | Asn | Arg | Ser | Ala | His |
|     |     |     |     | 245 |     |     |     |     | 250 |     |     |     |     | 255 |     |
| Asn | Ser | Arg | Val | Tyr | Gly | Leu | Lys | Ala | Thr | Asp | Val | Pro | Met | Ile | Leu |
|     |     |     | 260 |     |     |     |     | 265 |     |     |     |     | 270 |     |     |
| Lys | Lys | His | His | Val | Thr | Ile | Phe | Leu | Asp | Asn | Lys | Ser | Lys | Asn | Ile |
|     |     | 275 |     |     |     |     | 280 |     |     |     |     | 285 |     |     |     |
| Gly | Ser | Pro | Leu | Leu | Phe | Gly | Thr | Leu | Tyr | Val | Ile | Lys | His | Leu | Phe |
|     | 290 |     |     |     |     | 295 |     |     |     |     | 300 |     |     |     |     |
| Met | Tyr | Glu | Asn | Asp | His | Ile | Lys | Glu | Asn | Trp | Asn | Asn | Phe | Ile | Tyr |
| 305 |     |     |     |     | 310 |     |     |     |     | 315 |     |     |     |     | 320 |
| Lys | Leu | Asn | Asp | Lys | Leu | Leu | Glu | Ile | Lys | Lys | Ile | Glu | Lys | Ser | Gln |
|     |     |     |     | 325 |     |     |     |     | 330 |     |     |     |     | 335 |     |
| Tyr | Gly | Phe | Ser | Glu | Asp | Trp | Val | Lys | Gln | Leu | Glu | Ile | Ile | Asp |     |
|     |     |     | 340 |     |     |     |     | 345 |     |     |     |     | 350 |     |     |

( 2 ) INFORMATION FOR SEQ ID NO: 13:

( i ) SEQUENCE CHARACTERISTICS:
        ( A ) LENGTH: 2383 base pairs
        ( B ) TYPE: nucleic acid
        ( C ) STRANDEDNESS: double
        ( D ) TOPOLOGY: circular ( i i ) MOLECULE TYPE: DNA (genomic)

( i i i ) HYPOTHETICAL: NO ( v i ) ORIGINAL SOURCE:
        ( A ) ORGANISM: Lactococcus lactis
        ( B ) STRAIN: IL420

( i x ) FEATURE:
        ( A ) NAME/KEY: RBS
        ( B ) LOCATION: 268..275

( i x ) FEATURE:
        ( A ) NAME/KEY: CDS
        ( B ) LOCATION: 283..864

( i x ) FEATURE:
        ( A ) NAME/KEY: RBS
        ( B ) LOCATION: 863..871

( i x ) FEATURE:
        ( A ) NAME/KEY: CDS
        ( B ) LOCATION: 880..1614

( x i ) SEQUENCE DESCRIPTION: SEQ ID NO: 13:

```
GATCTAAAAC CAGTAAATAT TTTATATCCC AAAATTAGAA GAACAACAAA AAATCGGTTC        60

ATTCTTCAAA CAACTAGATA CACTATCGTT CTTCATCAAC GTAAGTTAGA TTTTTTGAAA       120

GAGCAGAAAA AAGGCTTTTT ACAAAGATG TTTGTTTAGG GTCTATAATT AGATAATAAC        180

CCCTCACAAA TCCCATTAAA ATAGCCCCTA AGATCTAACC TTTATATCTT AGGGGCTATT       240

TTTTGTTGT AATGATATAA TAACTCTAAA AGGAGTAAGC AA ATG AAT AAT GTT           294
                                                 Met Asn Asn Val
                                                   1

TTT AAA CCC ATT AAG TAT TTA AGT ATC ATT ATG CTT GTT GTT ATT ATC         342
Phe Lys Pro Ile Lys Tyr Leu Ser Ile Ile Met Leu Val Val Ile Ile
  5              10                 15                  20

TCA GCT GTA ATA ACT TAT ATT GTC AAT CCT AAT TTC TCA GAT ACA TTA         390
Ser Ala Val Ile Thr Tyr Ile Val Asn Pro Asn Phe Ser Asp Thr Leu
             25                 30                 35

AAT TCT GTA TCA AGT AAT ATT TCC AAA TCG GTC TCA CAG AAA TCA GGA         438
Asn Ser Val Ser Ser Asn Ile Ser Lys Ser Val Ser Gln Lys Ser Gly
```

-continued

|  |  |  | 40 |  |  |  |  | 45 |  |  |  |  | 50 |  |  |  |
|---|---|---|---|---|---|---|---|---|---|---|---|---|---|---|---|---|
| TTA | AAT | TTA | GTT | GTT | GCT | TAT | ATT | TTT | AAC | AAT | GGA | TTT | AAA | GTC | CCA | 486 |
| Leu | Asn | Leu | Val | Val | Ala | Tyr | Ile | Phe | Asn | Asn | Gly | Phe | Lys | Val | Pro |  |
|  |  | 55 |  |  |  |  | 60 |  |  |  |  | 65 |  |  |  |  |
| ATG | GGG | ATG | TTA | TTT | TTT | TCA | ATT | ATA | CCT | ATT | CGA | TTT | TTA | TAT | TGG | 534 |
| Met | Gly | Met | Leu | Phe | Phe | Ser | Ile | Ile | Pro | Ile | Arg | Phe | Leu | Tyr | Trp |  |
|  | 70 |  |  |  |  | 75 |  |  |  |  | 80 |  |  |  |  |  |
| ATT | CAG | CCA | CTT | TTC | ACA | GCC | ATA | TTA | CCT | GGA | ATT | TTA | TTT | GGG | ATA | 582 |
| Ile | Gln | Pro | Leu | Phe | Thr | Ala | Ile | Leu | Pro | Gly | Ile | Leu | Phe | Gly | Ile |  |
| 85 |  |  |  |  | 90 |  |  |  |  | 95 |  |  |  |  | 100 |  |
| GCA | TTT | AGA | TAC | TCG | GTT | GCA | AAA | GCT | TTT | ATC | ATA | TTA | ATT | TCT | TCA | 630 |
| Ala | Phe | Arg | Tyr | Ser | Val | Ala | Lys | Ala | Phe | Ile | Ile | Leu | Ile | Ser | Ser |  |
|  |  |  | 105 |  |  |  |  | 110 |  |  |  |  | 115 |  |  |  |
| CTA | CCT | CAT | ATG | TTA | TTA | GAG | ATA | TTC | GCA | TTT | TGC | TTA | TGG | ATG | GTC | 678 |
| Leu | Pro | His | Met | Leu | Leu | Glu | Ile | Phe | Ala | Phe | Cys | Leu | Trp | Met | Val |  |
|  |  |  | 120 |  |  |  |  | 125 |  |  |  |  | 130 |  |  |  |
| GCT | CTT | GAT | CGT | TTT | AAC | AAA | TGG | ATT | AGA | TAC | AAA | ATA | TCT | AGG | AAA | 726 |
| Ala | Leu | Asp | Arg | Phe | Asn | Lys | Trp | Ile | Arg | Tyr | Lys | Ile | Ser | Arg | Lys |  |
|  |  | 135 |  |  |  |  | 140 |  |  |  |  | 145 |  |  |  |  |
| AAA | CAA | ACA | AAT | ACT | AAG | TTA | TTT | TAT | GAA | TTC | AAG | TTA | ATA | TTA | ATC | 774 |
| Lys | Gln | Thr | Asn | Thr | Lys | Leu | Phe | Tyr | Glu | Phe | Lys | Leu | Ile | Leu | Ile |  |
| 150 |  |  |  |  | 155 |  |  |  |  | 160 |  |  |  |  |  |  |
| TCA | TAT | GTT | AAG | TAC | GTT | ATC | CCA | TTA | ATT | GTT | ATC | GCA | GCT | TTT | ACT | 822 |
| Ser | Tyr | Val | Lys | Tyr | Val | Ile | Pro | Leu | Ile | Val | Ile | Ala | Ala | Phe | Thr |  |
| 165 |  |  |  | 170 |  |  |  |  | 175 |  |  |  |  | 180 |  |  |
| GAA | ACT | TAT | GTT | GCG | GAT | TGG | ATT | AGT | CAT | ATA | TTA | AGT | TAAAAAGGA |  |  | 871 |
| Glu | Thr | Tyr | Val | Ala | Asp | Trp | Ile | Ser | His | Ile | Leu | Ser |  |  |  |  |
|  |  |  |  | 185 |  |  |  |  | 190 |  |  |  |  |  |  |  |
| AGAGTATT | ATG | GAT | ATT | TTA | TTT | TTA | GAA | AAA | GCA | TTG | ACC | AAT | TCT | GAT |  | 921 |
|  | Met | Asp | Ile | Leu | Phe | Leu | Glu | Lys | Ala | Leu | Thr | Asn | Ser | Asp |  |  |
|  | 1 |  |  | 5 |  |  |  |  | 10 |  |  |  |  |  |  |  |
| TGG | TTA | GGT | TTT | TTG | GGG | AAT | ATT | GTA | AGT | GGT | ATA | ATT | GGG | CTA | ATT | 969 |
| Trp | Leu | Gly | Phe | Leu | Gly | Asn | Ile | Val | Ser | Gly | Ile | Ile | Gly | Leu | Ile |  |
| 15 |  |  |  | 20 |  |  |  |  | 25 |  |  |  |  | 30 |  |  |
| GGA | GCT | GGA | TTA | GGT | GTC | TAT | GGA | GCA | TAC | TCA | GTG | ATG | CAA | AAA | CAA | 1017 |
| Gly | Ala | Gly | Leu | Gly | Val | Tyr | Gly | Ala | Tyr | Ser | Val | Met | Gln | Lys | Gln |  |
|  |  |  | 35 |  |  |  |  | 40 |  |  |  |  | 45 |  |  |  |
| TTA | AAA | GTA | GAG | AAT | GAA | AAG | TAT | AGA | AAA | GAT | AGA | ATT | GAT | AAT | ACT | 1065 |
| Leu | Lys | Val | Glu | Asn | Glu | Lys | Tyr | Arg | Lys | Asp | Arg | Ile | Asp | Asn | Thr |  |
|  |  |  | 50 |  |  |  |  | 55 |  |  |  |  | 60 |  |  |  |
| TTT | TTC | AAT | TTA | TTG | GGT | TTG | TTT | CAG | AAT | GTA | CGA | GAG | GAA | TTA | GAT | 1113 |
| Phe | Phe | Asn | Leu | Leu | Gly | Leu | Phe | Gln | Asn | Val | Arg | Glu | Glu | Leu | Asp |  |
|  |  | 65 |  |  |  |  | 70 |  |  |  |  | 75 |  |  |  |  |
| TCG | AGT | GAA | ATT | ATT | AGT | GAT | ATA | AAA | TCC | TTA | AGA | CGT | CTT | AAA | ATC | 1161 |
| Ser | Ser | Glu | Ile | Ile | Ser | Asp | Ile | Lys | Ser | Leu | Arg | Arg | Leu | Lys | Ile |  |
|  | 80 |  |  |  |  | 85 |  |  |  |  | 90 |  |  |  |  |  |
| GGA | GAA | GAC | CCA | TAC | TCC | ATT | TTT | ACA | TCA | ATA | GAC | GTA | AAT | AAT | ATA | 1209 |
| Gly | Glu | Asp | Pro | Tyr | Ser | Ile | Phe | Thr | Ser | Ile | Asp | Val | Asn | Asn | Ile |  |
| 95 |  |  |  |  | 100 |  |  |  |  | 105 |  |  |  |  | 110 |  |
| ATA | AAT | AAA | CAG | GAT | GAT | ATT | GTT | GAA | ATT | ATA | AAC | GAA | GTA | TTT | AAA | 1257 |
| Ile | Asn | Lys | Gln | Asp | Asp | Ile | Val | Glu | Ile | Ile | Asn | Glu | Val | Phe | Lys |  |
|  |  |  | 115 |  |  |  |  | 120 |  |  |  |  | 125 |  |  |  |
| TCT | AAT | AAA | AAT | TAC | TCT | GGA | AAT | TAT | TTT | AGA | GCT | TTA | TAC | AGA | TGT | 1305 |
| Ser | Asn | Lys | Asn | Tyr | Ser | Gly | Asn | Tyr | Phe | Arg | Ala | Leu | Tyr | Arg | Cys |  |
|  |  | 130 |  |  |  |  | 135 |  |  |  |  | 140 |  |  |  |  |
| TTA | AAA | TAT | ATT | ATC | GAT | TCT | GAT | TTA | AAA | ATG | GAA | GAT | AAA | AAG | TTT | 1353 |
| Leu | Lys | Tyr | Ile | Ile | Asp | Ser | Asp | Leu | Lys | Met | Glu | Asp | Lys | Lys | Phe |  |
|  |  | 145 |  |  |  |  | 150 |  |  |  |  | 155 |  |  |  |  |
| TAT | TCA | GGA | GTG | CTT | AGA | GGG | ATT | CTA | TCA | TCT | AAG | GAA | ATG | TTA | GTA | 1401 |
| Tyr | Ser | Gly | Val | Leu | Arg | Gly | Ile | Leu | Ser | Ser | Lys | Glu | Met | Leu | Val |  |

-continued

```
           160                           165                           170
GTG  TTT  TAT  AAT  TGC  ATG  TAT  TTT  GAA  AAA  GGT  AAG  AAA  TTC  AAA  GAA          1449
Val  Phe  Tyr  Asn  Cys  Met  Tyr  Phe  Glu  Lys  Gly  Lys  Lys  Phe  Lys  Glu
175                 180                           185                           190

CTA  CTT  GAA  AAA  AAA  GAG  AAT  GGT  AAA  AGA  ATT  GAC  TTT  TTT  GGT  GAT          1497
Leu  Leu  Glu  Lys  Lys  Glu  Asn  Gly  Lys  Arg  Ile  Asp  Phe  Phe  Gly  Asp
                    195                           200                           205

AAA  GAA  GAT  TTG  AAA  AAC  TTG  GAT  AAA  GGA  AAT  GAC  CTA  CCT  TTC  TTT          1545
Lys  Glu  Asp  Leu  Lys  Asn  Leu  Asp  Lys  Gly  Asn  Asp  Leu  Pro  Phe  Phe
                    210                           215                           220

GGT  AAA  GAG  GAT  TTA  TTA  TTT  TCG  AAA  ACC  GAT  ATG  CAA  AAA  TTA  GAG          1593
Gly  Lys  Glu  Asp  Leu  Leu  Phe  Ser  Lys  Thr  Asp  Met  Gln  Lys  Leu  Glu
          225                           230                           235

GAA  CTT  ATA  AAA  GGA  AAC  TAGAGGTTTT  CTTTTTTGT  TTATTGATTT                          1641
Glu  Leu  Ile  Lys  Gly  Asn
240                 245

CTCTTAAATT  AAGTACAAGT  AAAATGCTAA  TTTACAATA   CACCCAAACA  CAAGATGTTG                   1701

TGTTTAGTTA  CAAACTCAAA  CACTATATGT  AGTGTCTAAA  AATTATCTTT  CATTCTGGTG                   1761

CAACTACGAC  TATAAAAAAT  TCGACTTTCT  ACTATTGAT   GTTATCCTTA  AATCTTAGAG                   1821

TCACTATTGT  ATAATTTAGA  CTAAGGACAA  AATGGACTAT  TATCAAATAA  ATAGACATAA                   1881

AAAGAAAATC  GTTCTGATCG  TTTTTCCTTT  TTATCTGAT   GTTCAGAAAA  TGGTCATTTT                   1941

CTGGACACTC  TTCTTTTGTT  ATAAAAACTC  TCAAGATCAT  TTACATTTCT  TGTTCATTAA                   2001

CCCGTAATTT  ATTCTATGTT  CATTTATATA  AGTGCTTTCA  GGTTATGGTA  CAATAGTATC                   2061

AATGGAGGAA  TAAAGACGTA  AAGCTTCTTA  AGACATTGGT  AGAAAGTGGA  ACACCAATTA                   2121

AATCGATTGC  GGATTCTTGA  GGAGTTTCTA  GAACAACAAT  TTATAGATAT  ATTAATAAAC                   2181

CCGAATTGCT  AGTTGATTAT  TTAGCCATGA  CTTGATACCC  GATAGAATAT  CTTAGAGTCT                   2241

TTAGAATTTC  TGTAGTGAAA  TCGTTCATAT  GGAAGTCCTC  TTTTCTGTGA  ATGTGTTGTG                   2301

GTAACTCTAT  TCTACAGAAG  GGACTTCCTT  TTTTCTATTT  ACACAAAATA  TTTTACACTC                   2361

TCCTACTTGA  AGTTTCCGAA  TG                                                               2383
```

(2) INFORMATION FOR SEQ ID NO: 14:

(i) SEQUENCE CHARACTERISTICS:
        (A) LENGTH: 193 amino acids
        (B) TYPE: amino acid
        (D) TOPOLOGY: linear (ii) MOLECULE TYPE: protein (xi) SEQUENCE DESCRIPTION: SEQ ID NO: 14:

```
Met  Asn  Asn  Val  Phe  Lys  Pro  Ile  Lys  Tyr  Leu  Ser  Ile  Ile  Met  Leu
1                   5                        10                       15

Val  Val  Ile  Ile  Ser  Ala  Val  Ile  Thr  Tyr  Ile  Val  Asn  Pro  Asn  Phe
               20                       25                       30

Ser  Asp  Thr  Leu  Asn  Ser  Val  Ser  Ser  Asn  Ile  Ser  Lys  Ser  Val  Ser
          35                       40                       45

Gln  Lys  Ser  Gly  Leu  Asn  Leu  Val  Val  Ala  Tyr  Ile  Phe  Asn  Asn  Gly
     50                       55                       60

Phe  Lys  Val  Pro  Met  Gly  Met  Leu  Phe  Phe  Ser  Ile  Ile  Pro  Ile  Arg
65                       70                       75                       80

Phe  Leu  Tyr  Trp  Ile  Gln  Pro  Leu  Phe  Thr  Ala  Ile  Leu  Pro  Gly  Ile
               85                       90                       95

Leu  Phe  Gly  Ile  Ala  Phe  Arg  Tyr  Ser  Val  Ala  Lys  Ala  Phe  Ile  Ile
               100                      105                      110
```

```
Leu  Ile  Ser  Ser  Leu  Pro  His  Met  Leu  Leu  Glu  Ile  Phe  Ala  Phe  Cys
          115                      120                     125

Leu  Trp  Met  Val  Ala  Leu  Asp  Arg  Phe  Asn  Lys  Trp  Ile  Arg  Tyr  Lys
     130                      135                     140

Ile  Ser  Arg  Lys  Lys  Gln  Thr  Asn  Thr  Lys  Leu  Phe  Tyr  Glu  Phe  Lys
145                      150                      155                          160

Leu  Ile  Leu  Ile  Ser  Tyr  Val  Lys  Tyr  Val  Ile  Pro  Leu  Ile  Val  Ile
                    165                      170                     175

Ala  Ala  Phe  Thr  Glu  Thr  Tyr  Val  Ala  Asp  Trp  Ile  Ser  His  Ile  Leu
               180                      185                          190

Ser
```

(2) INFORMATION FOR SEQ ID NO: 15:

(i) SEQUENCE CHARACTERISTICS:
      (A) LENGTH: 244 amino acids
      (B) TYPE: amino acid
      (D) TOPOLOGY: linear (ii) MOLECULE TYPE: protein (xi) SEQUENCE DESCRIPTION: SEQ ID NO: 15:

```
Met  Asp  Ile  Leu  Phe  Leu  Glu  Lys  Ala  Leu  Thr  Asn  Ser  Asp  Trp  Leu
1                   5                    10                          15

Gly  Phe  Leu  Gly  Asn  Ile  Val  Ser  Gly  Ile  Ile  Gly  Leu  Ile  Gly  Ala
               20                   25                          30

Gly  Leu  Gly  Val  Tyr  Gly  Ala  Tyr  Ser  Val  Met  Gln  Lys  Gln  Leu  Lys
          35                   40                          45

Val  Glu  Asn  Glu  Lys  Tyr  Arg  Lys  Asp  Arg  Ile  Asp  Asn  Thr  Phe  Phe
     50                   55                        60

Asn  Leu  Leu  Gly  Leu  Phe  Gln  Asn  Val  Arg  Glu  Glu  Leu  Asp  Ser  Ser
65                   70                   75                               80

Glu  Ile  Ile  Ser  Asp  Ile  Lys  Ser  Leu  Arg  Arg  Leu  Lys  Ile  Gly  Glu
               85                        90                              95

Asp  Pro  Tyr  Ser  Ile  Phe  Thr  Ser  Ile  Asp  Val  Asn  Asn  Ile  Ile  Asn
               100                      105                     110

Lys  Gln  Asp  Asp  Ile  Val  Glu  Ile  Ile  Asn  Glu  Val  Phe  Lys  Ser  Asn
          115                      120                     125

Lys  Asn  Tyr  Ser  Gly  Asn  Tyr  Phe  Arg  Ala  Leu  Tyr  Arg  Cys  Leu  Lys
     130                      135                     140

Tyr  Ile  Ile  Asp  Ser  Asp  Leu  Lys  Met  Glu  Asp  Lys  Lys  Phe  Tyr  Ser
145                      150                     155                          160

Gly  Val  Leu  Arg  Gly  Ile  Leu  Ser  Ser  Lys  Glu  Met  Leu  Val  Val  Phe
               165                      170                     175

Tyr  Asn  Cys  Met  Tyr  Phe  Glu  Lys  Gly  Lys  Lys  Phe  Lys  Glu  Leu  Leu
               180                      185                     190

Glu  Lys  Lys  Glu  Asn  Gly  Lys  Arg  Ile  Asp  Phe  Phe  Gly  Asp  Lys  Glu
          195                      200                     205

Asp  Leu  Lys  Asn  Leu  Asp  Lys  Gly  Asn  Asp  Leu  Pro  Phe  Phe  Gly  Lys
     210                      215                     220

Glu  Asp  Leu  Leu  Phe  Ser  Lys  Thr  Asp  Met  Gln  Lys  Leu  Glu  Glu  Leu
225                      230                     235                          240

Ile  Lys  Gly  Asn
```